(12) United States Patent
Cook et al.

(10) Patent No.: US 6,172,052 B1
(45) Date of Patent: Jan. 9, 2001

(54) 17β-ACYL-17α-PROPYNYL-11β-ARYLSTEROIDS AND THEIR DERIVATIVES HAVING AGONIST OR ANTAGONIST HORMONAL PROPERTIES

(75) Inventors: C. Edgar Cook, Staunton, VA (US); John A. Kepler, Raleigh; Jill M. O'Reilly, Durham, both of NC (US)

(73) Assignee: Research Triangle Institute, Research Triangle Park, NC (US)

( * ) Notice: Under 35 U.S.C. 154(b), the term of this patent shall be extended for 0 days.

(21) Appl. No.: 09/205,395

(22) Filed: Dec. 4, 1998

(51) Int. Cl.[7] ............... C07J 17/00; A61K 31/58

(52) U.S. Cl. .................. 514/169; 552/608; 552/520; 514/169; 514/177; 514/179

(58) Field of Search ................... 514/169, 177, 514/179; 552/520, 605, 608

(56) References Cited

U.S. PATENT DOCUMENTS

| | | | |
|---|---|---|---|
| 4,954,490 | * 9/1990 | Cook et al. | 514/176 |
| 5,047,928 | * 9/1991 | Kasch et al. | 514/179 |
| 5,073,548 | 12/1991 | Cook, et al. | 514/167 |
| 5,407,928 | 4/1995 | Kasch, et al. | 514/179 |
| 5,981,516 | 11/1999 | Bouali, et al. | 514/176 |
| 6,020,328 | 2/2000 | Cook, et al. | 514/176 |

FOREIGN PATENT DOCUMENTS

| | | |
|---|---|---|
| EP 411733 | 2/1991 | (EP) . |
| EP 446124 | 9/1991 | (EP) . |

\* cited by examiner

*Primary Examiner*—Jose' G. Dees
*Assistant Examiner*—Sabiha Qazi
(74) *Attorney, Agent, or Firm*—Oblon, Spivak, McClelland, Maier & Neustadt, P.C.

(57) ABSTRACT

The invention is directed to a novel class of 17β-acyl-17β-propynyl steroids which exhibit potent antiprogestational activity.

5 Claims, 2 Drawing Sheets

CHART 1, Part I

Synthesis of 17α-Propynyl Compounds

17β-ACYL-17α-PROPYNYL-11β-ARYLSTEROIDS AND THEIR DERIVATIVES HAVING AGONIST OR ANTAGONIST HORMONAL PROPERTIES

BACKGROUND OF THE INVENTION

1. Field of the Invention

This invention relates to a novel class of 17β-acyl-17α-propynyl steroids which are believed to bind to the progestin receptor and which exhibit potent antiprogestational activity. Such compounds are useful for treatment of fibroids, endometriosis, and certain tumors, in causing cervical ripening prior to delivery, in hormone replacement therapy and in control of fertility and reproduction.

2. Discussion of the Background

Progesterone plays a major role in reproductive health and functioning. Its effects on, for example, the uterus, breast, cervix and hypothalamic-pituitary unit are well established. It also has extra-reproductive activities that are less well studied, such as effects on the brain, the immune system, the vascular endothelial system and on lipid metabolism. Given this wide array of effects, it is apparent that compounds which mimic some of the effects of progesterone (agonists), antagonize these effects (antagonists) or exhibit mixed effects (partial agonists or mixed agonist/antagonist) can be useful in treating a variety of disease states and conditions.

Steroid hormones exert their effects, in-part, by binding to intracellular receptors. Compounds that bind to the appropriate receptors and are antagonists or partial agonists of the estrogenic and androgenic hormones have long been known, but it was not until around 1982 that the discovery of compounds that bind to the progesterone receptor and antagonize the effects of progesterone was announced. Since then, a number of such compounds have been reported in the scientific and patent literature and their effects in vitro, in animals and in humans have been studied. Although compounds such as estrogens and certain enzyme inhibitors can prevent the physiological effects of endogenous progesterone, in this discussion "antiprogestin" is confined to those compounds that bind to the progestin receptor.

Information indicating that antiprogestins would be effective in a number of medical conditions is now available. This information has been summarized in a report from the Institute of Medicine (Donaldson, Molly S.; Dorflinger, L.; Brown, Sarah S.; Benet, Leslie Z., Editors, *Clinical Applications of Mifepristone (RU 486) and Other Antiprogestins*, Committee on Antiprogestins: Assessing the Science, Institute of Medicine, National Academy Press, 1993). In view of the pivotal role that progesterone plays in reproduction, it is not surprising that antiprogestins could play a part in fertility control, including 1-5 contraception (long-term and emergency or post-coital), menses induction and medical termination of pregnancy, but there are many other potential uses that have been supported by small clinical or preclinical studies. Among these are the following:

1. Labor and delivery—antiprogestins may be used for cervical ripening prior to labor induction such as at term or when labor must be induced due to fetal death. They may also be used to help induce labor in term or post-term pregnancies.
2. Treatment of uterine leiomyomas (fibroids)—these non-malignant tumors may affect up to 20% of women over 30 years old and are one of the most common reasons for surgery in women during their reproductive years. Hysterectomy, the common treatment for persistent symptoms, of course results in sterility.
3. Treatment of endometriosis—this common (5 to 15% incidence, much larger in infertile women) and often painful condition is now treated with drugs such as danazol or gonadotrophin-releasing hormnone analogs that have significant side-effects, or must be dealt with surgically.
4. Hormone replacement therapy, where they may be given to interupt or curtail the activity of pro gestins.
5. Cancers, particularly breast cancers—the presence of progestin receptors in many breast cancers has suggested the use of antiprogestins in treating metastatic cancer or in prevention of recurrence or initial development of cancer.
6. Other tumors such as meningiomas—these brain membrane tumors, although non-malignant, result in death of the patient and nonsurgical treatments are lacking.
7. Male contraception—antiprogestins can interfere with sperm viability, although whether this is an antiprogestational effect or not is controversial, as it may relate to the antiglucocorticoid activity of such compounds.
8. Antiestrogenic effects—at least some antiprogestins oppose the action of estrogens in certain tests, but apparently through a mechanism that does not involve classical hormone receptors. This opens a variety of possibilities for their medical use.
9. Anti glucocorticoid effects—this is a common side-effect of antiprogestins, which can be useful in some instances, such as the treatment of Cushing's syndrome, and could play a role in immune disorders, for example. In other instances it is desirable to minimize such effects.

The effects and uses of progesterone agonists have been well documented. In addition, it has been recently shown that certain compounds structurally related to the known antiprogestins have strong agonist activity in certain biological systems (e.g., the classical progestin effects in the estrogen-primed immature rabbit uterus; cf. C. E. Cook et al., Life Sciences, 52, 155–162 (1993)). Such compounds are partial agonists in human cell-derived receptor systems, where they bind to a site distinct from both the progestin and antiprogestin sites (Wagner et al., Proc. Natl. Acad. Sci., 93, 8739–8744 (1996)). Thus the general class of antiprogestins can have subclasses, which may vary in their clinical profiles.

Generally antiprogestational activity has been associated with the presence of an 11β-aryl substituent on the steroid nucleus, together with a $\Delta^{4,9}$-3-ketone or $\Delta^{4}$-3-ketone moiety. However, it has been shown that substituents on the D-ring of the steroid can have a marked influence on the biological profile of these compounds (see above). The earliest antiprogestins were substituted with a 17β-hydroxyl group and various 17α-substituents. (See for example, Teutsch, Jean G.; Costerousse, Germain; Philibert, Daniel, and Deraedt, Roger. Novel steroids. U.S. Pat. No. 4,386,085. 1983; Philibert, Daniel; Teutsch, Jean G.; Costerousse, Germain, and Deraedt, Roger. 3-Keto-19-nor-Δ-4,9-steroids. U.S. Pat. No. 4,477,445. 1983; Teutsch, Jean G.; Pantin, Germain; Costerousse, Saint-Maurice; Daniel Philibert; La Varenne Saint Hilaire; Roger Deraedt, inventors. Steroid derivatives. Roussel Uclaf, assignee. U.S. Pat. No. 4,447,424. 1984; Cook, C. Edgar; Tallent, C. Ray; Reel, Jerry R., and Wani, Mansukh C. 17α-(Substituted-methyl)-17β-hydroxy/esterified hydroxy steroids and pharmaceutical compositions containing them. U.S. Pat. Nos. 4,774,236 (1988) and 4,861,763 (1989)). Then it was discovered that a 17β-acetyl, 17α-acyloxy group could also generate antiprogestational effects (Cook, C. Edgar; Lee, Y.-W.; Reel, Jerry R.; Wani, Mansukh C., Rector, Douglas. 11β-Substituted Progesterone Analogs. U.S. Pat. Nos. 4,954,490 (1990) and 5,073,548 (1991)), and various permutations of these findings have been made as well. However, introduction of a 16α-ethyl group or a hydrogen substituent at the 17α-position in the 17β-acyl series of compounds leads to agonist or partial agonist activity (C. E. Cook et al., Life Sciences, 52, 155–162 (1993)). Thus changes in the D-ring of the steroid result in a wide variety of effects on the biological activity. Accordingly there remains a need for antiprogestin compounds which exhibit higher specificity.

Cook et al. U.S. Pat. No. 5,073,548 report 17α-alkynyl-11β-(substituted phenyl)-19-norpregna-4,9-diene-3,20-dione compounds but fail to exemplify 17β-acyl-17α-propyn-1-yl compounds.

Cook et al., in co-pending U.S. Ser. No. 09/035,949, filed on Mar. 16, 1998, report 17β-acyl-11β-cyclicaminophenyl steroids.

It is therefore the purpose of the present invention to provide novel and potent progestin antagonists (antiprogestins) and mixed or partial progestin agonists, to provide methods for their medical use in mammals, including humans, and to provide methods for their synthesis.

In spite of the clinical promise of antiprogestins, as of Nov. 1, 1998, there were no antiprogestin drugs marketed in the United States or many other countries. Only one antiprogestin drug is approved and available for clinical use anywhere in the world and that drug, mifepristone, is mainly used for medical termination of pregnancy. A number of factors are the cause of this situation, but certainly a need exists for new antiprogestational drugs that can be used for the conditions described above.

It is therefore the purpose of the present invention to provide novel and potent progestin antagonists (antiprogestins) and mixed or partial progestin agonists, and to provide methods for their medical use in mammals, including humans.

SUMMARY OF THE INVENTION

This invention provides a group of novel 17β- acyl-17α-propynyl steroids, which are characterized by 11β-(4-substituted phenyl) substitution.

According to one embodiment of the present invention is a hormonal or antihormonal steroid compound of structure I, (I)

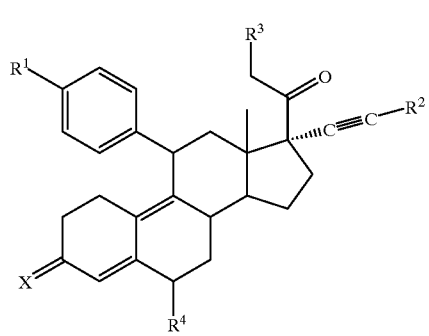

where
$R^1$ is $(CH_3)_2N—$, $CH_3NH—$, $NH_2—$;
$R^2$ is $CH_3—$, $CF_3—$, $HOCH_2—$;
$R^3$ is $H—$, $CH_3—$, $CH_3O—$, $CH_3COO—$;
$R^4$ is $H—$, $CH_3—$, $F—$, $Cl—$; and X is O, (H,H), NOH, $NOCH_3$, and pharmaceutically acceptable salts thereof.

According to another embodiment of the present invention is a hormonal or antihormonal steroid compound of structure II, (II)

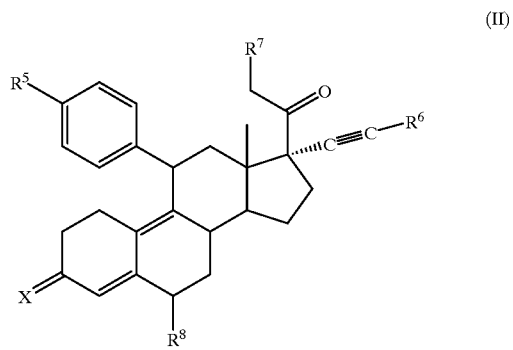

where $R^5$ is $CH_3CO—$, $CH_3S—$, $CH_3S(O)—$, $CH_3S(O)_2—$, $CH_3O—$;
$R^6$ is $CH_3—$, $CF_3—$, $HOCH_2—$;
$R^7$ is $H—$, $CH_3—$, $CH_3O—$, $CH_3COO—$;
$R^8$ is $H—$, $CH_3—$, $F—$, $Cl—$; and
X is O, (H,H), NOH, $NOCH_3$, and pharmaceutically acceptable salts thereof.

These and other objects of the present invention are made possible by the discovery that 17β-acyl-17α-propynyl-11β-(4-substituted phenyl) steroids exhibit exceptional agonist or antagonist hormonal activity.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
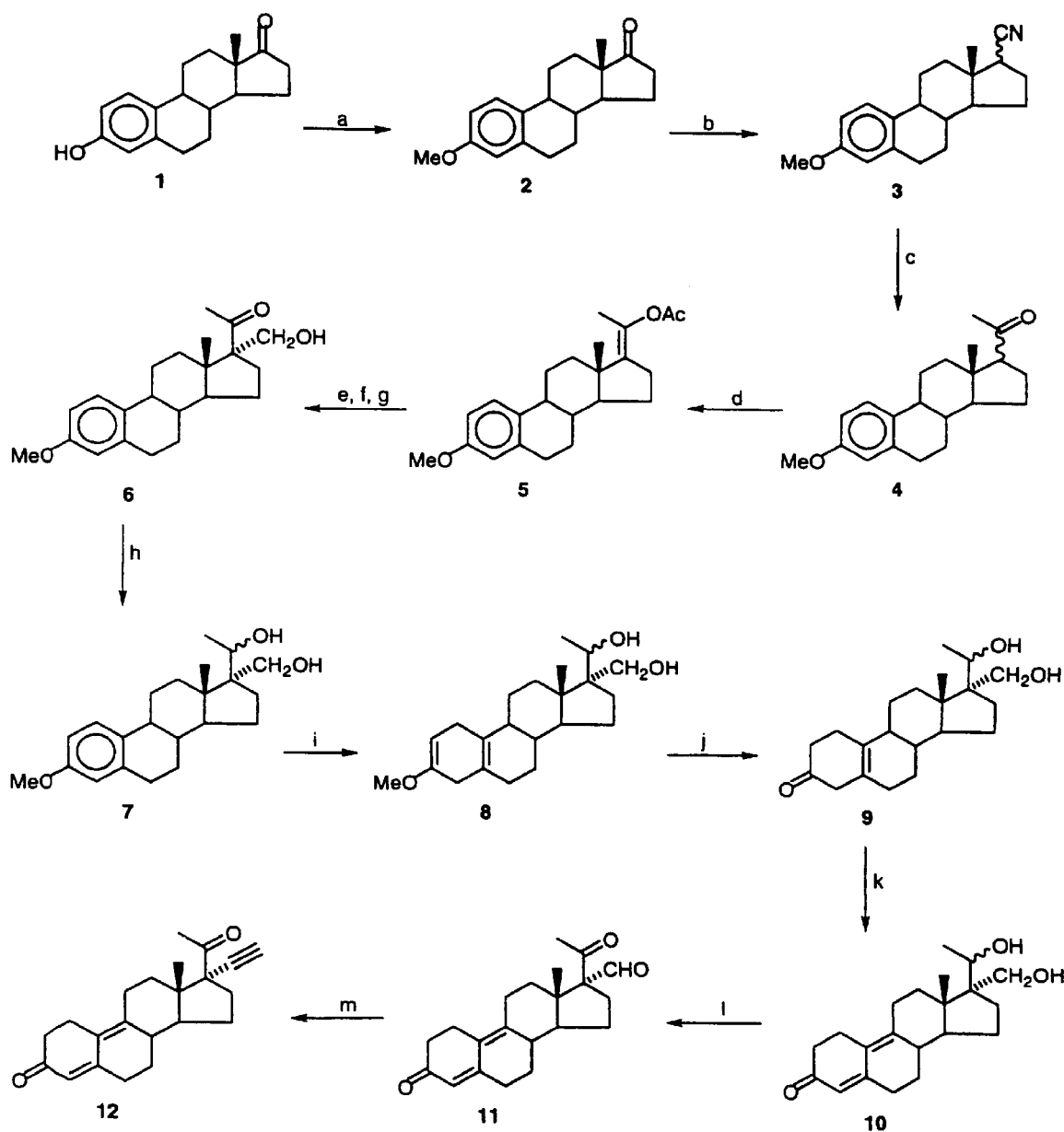
FIG. 1 depicts a reaction scheme to prepare 17β-acyl-17α-propynyl compounds according to the present invention.
Figure 1A:
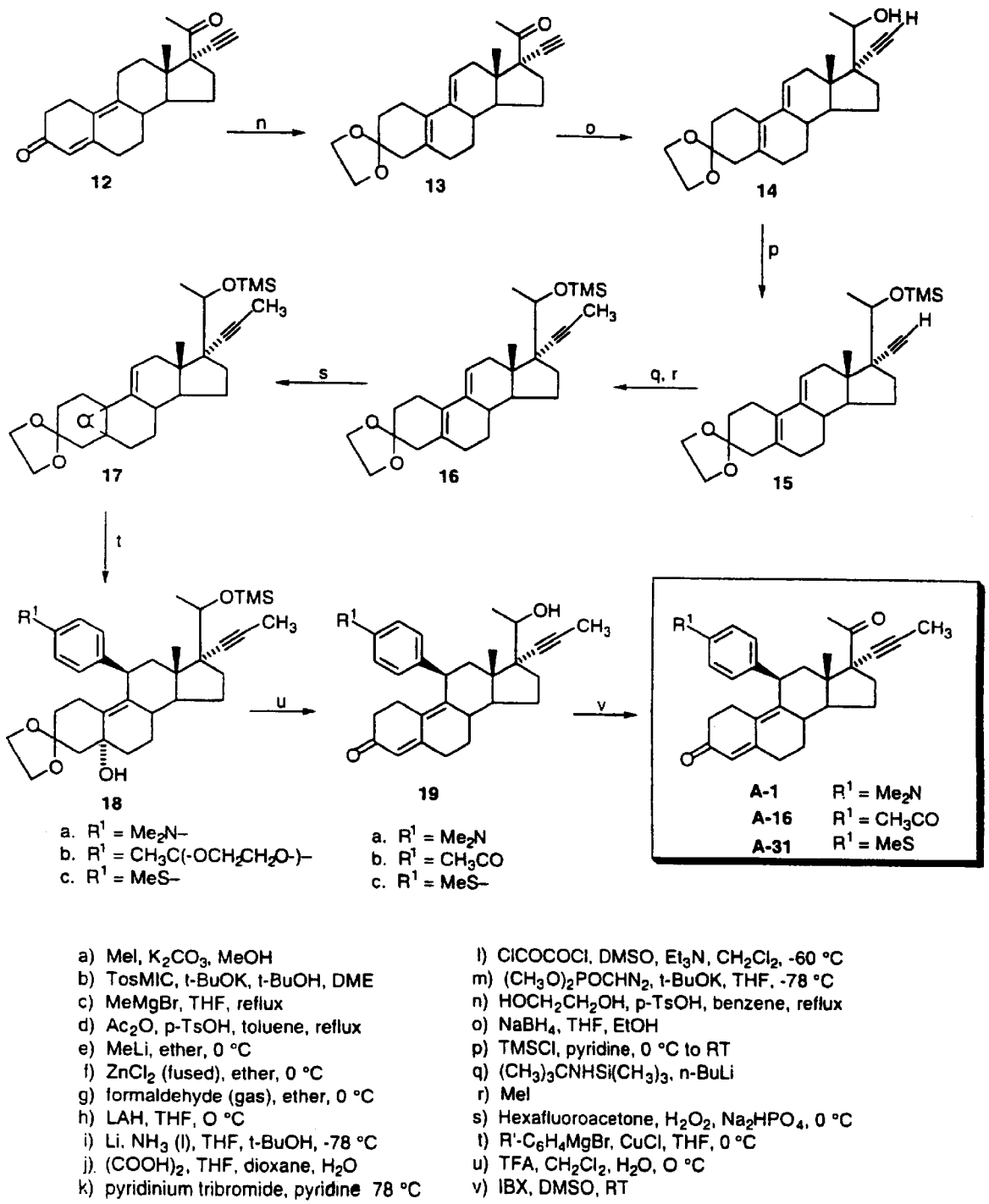

The above-identified compounds of formula I specifically include compounds which are substituted on the A ring at the 3-position with two hydrogen atoms. These compounds are believed to undergo oxidation in vivo to the corresponding carbonyl compound.

According to one embodiment of the present invention is a hormonal or antihormonal steroid compound of structure I,

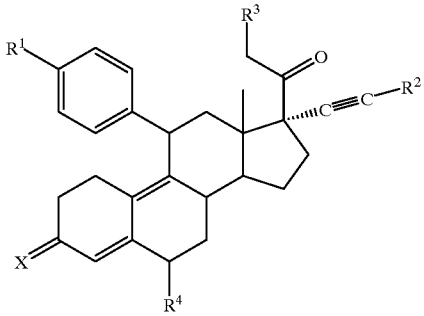

(I)

where

R¹ is $(CH_3)_2N-$, $CH_3NH-$, $NH_2-$;

R² is $CH_3-$, $CF_3-$, $HOCH_2-$;

R³ is $H-$, $CH_3-$, $CH_3O-$, $CH_3COO-$;

R⁴ is $H-$, $CH_3-$, $F-$, $Cl-$; and

X is O, (H,H), NOH, NOCH₃, and pharmaceutically acceptable salts thereof.

According to another embodiment of the present invention is a hormonal or antihormonal steroid compound of structure II,

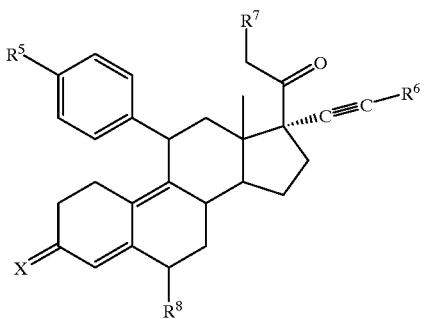

(II)

where

R⁵ is $CH_3CO-$, $CH_3S-$, $CH_3S(O)-$, $CH_3S(O)_2-$, $CH_3O-$;

R⁶ is $CH_3-$, $CF_3-$, $HOCH_2-$;

R⁷ is $H-$, $CH_3-$, $CH_3O-$, $CH_3COO-$;

R⁸ is $H-$, $CH_3-$, $F-$, $Cl-$; and

X is O, (H,H), NOH, NOCH₃, and pharmaceutically acceptable salts thereof.

Within the scope of the present invention are specifically 17α-(1-propynyl)-11β-(4-aminophenyl)-19-norpregna-4,9-diene-3,20-dione compounds of the formula (III)

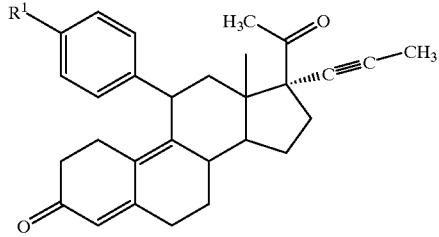

(III)

where
R¹ is $(CH_3)_2N-$, $CH_3NH-$, $NH_2-$.

A particularly preferred compound is of formula (IV)

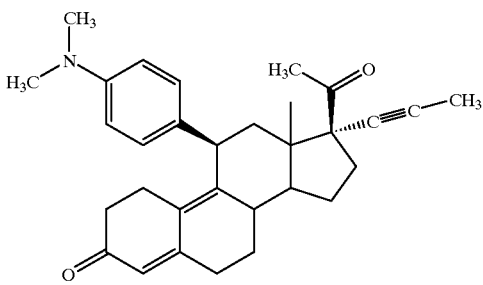

(IV)

The compounds of the present invention may also comprise a salt formed with the amine. Suitable pharmaceutically acceptable salts are known to those of ordinary skill in the art and comprise carboxylates, sulfates, phosphates and halides.

Within the context of the present invention, the group R⁴ in structure I and R⁸ is structure II may be in either the α or β stereochemical configuration.

Specific compounds of formula I are
1. 11β-(4-aminophenyl)-17α-(1-propynyl)-19-norpregna-4,9-diene-3,20-dione;
2. 11β-(4-aminophenyl)-17α-(3,3,3-trifluoropropyn-1-yl)-19-norpregna-4,9-diene-3,20-dione;
3. 11β-(4-aminophenyl)-17α-(3-hydroxypropyn-1-yl)-19-norpregna-4,9-diene-3,20-dione;
4. 11β-(4-aminophenyl)-21-methoxy-17α-(1-propynyl)-19-norpregna-4,9-diene-3,20-dione;
5 11β-(4-aminophenyl)-21-methoxy-17α-(3,3,3-trifluoropropyn-1-yl)-19-norpregna-4,9-diene-3,20-dione;
6. 11β-(4-aminophenyl)-21-methoxy-17α-(3-hydroxypropyn-1-yl)-19-norpregna- 4,9-diene-3,20-dione;
7. 11β-(4-aminophenyl)-21-methoxy-3-oximino-17α-(1-propynyl)-19-norpregna-4,9-diene-3,20-dione;
8. 11β-(4-aminophenyl)-21-methoxy-3-oximino-17α-(3,3,3-trifluoropropyn-1-yl)-19-norpregna-4,9-diene-3,20-dione;
9. 11β-(4-aminophenyl)-21-methoxy-3-oximino-17α-(3-hydroxypropyn-1-yl)-19-norpregna-4,9-diene-3,20-dione;
10. 11β-(4-aminophenyl)-21-methoxy-6-fluoro-17α-(1-propynyl)-19-norpregna-4,9-diene-3,20-dione;
11. 11β-(4-aminophenyl)-21-methoxy-6-fluoro-17α-(3,3,3-trifluoropropyn-1-yl)-19-norpregna-4,9-diene-3,20-dione;

12. 11β-(4-aminophenyl)-21-methoxy-6-fluoro-17α-(3-hydroxypropyn-1-yl)-19-norpregna-4,9-diene-3,20-dione;
13. 11β-(4-aminophenyl)-21-methoxy-6-fluoro-3-oximino-17α-(1-propynyl)-19-norpregna-4,9-diene-3,20-dione;
14. 11β-(4-aminophenyl)-21-methoxy-6-fluoro-3-oximino-17α-(3,3,3-trifluoropropyn-1-yl)-19-norpregna-4,9-diene-3,20-dione;
15. 11β-(4-aminophenyl)-21-methoxy-6-fluoro-3-oximino-17α-(3-hydroxypropyn-1-yl)-19-norpregna-4,9-diene-3,20-dione;
16. 11β-(4-aminophenyl)-21-methoxy-6-methyl-17α-(1-propynyl)-19-norpregna-4,9-diene-3,20-dione;
17. 11β-(4-arninophenyl)-21-methoxy-6-methyl-17α-(3,3,3-trifluoropropyn-1-yl)-19-norpregna-4,9-diene-3,20-dione;
18. 11β-(4-aminophenyl)-21-methoxy-6-methyl-17α-(3-hydroxypropyn-1-yl)-19-norpregna-4,9-diene-3,20-dione;
19. 11β-(4-aminophenyl)-21-methoxy-6-methyl-3-oximino-17α-(1-propynyl)-19-norpregna-4,9-diene-3,20-dione;
20. 11β-(4-aminophenyl)-21-methoxy-6-methyl-3-oximino-17α-(3,3,3-trifluoropropyn-1-yl)-19-norpregna-4,9-diene-3,20-dione;
21. 11β-(4-aminophenyl)-21-methoxy-6-methyl-3-oximino-17α-(3-hydroxypropyn-1-yl)-19-norpregna-4,9-diene-3,20-dione;
22. 11β-(4-aminophenyl)-21-methyl-17α-(1-propynyl)-19-norpregna-4,9-diene-3,20-dione;
23. 11β-(4-aminophenyl)-21-methyl-17α-(3,3,3-trifluoropropyn-1-yl)-19-norpregna-4,9-diene-3,20-dione;
24. 11β-(4-aminophenyl)-21-methyl-17α-(3-hydroxypropyn-1-yl)-19-norpregna-4,9-diene-3,20-dione;
25. 11β-(4-aminophenyl)-21-methyl-3-oximino-17α-(1-propynyl)-19-norpregna-4,9-diene-3,20-dione;
26. 11β-(4-aminophenyl)-21-methyl-3-oximino-17α-(3,3,3-trifluoropropyn-1-yl)-19-norpregna-4,9-diene-3,20-dione;
27. 11β-(4-aminophenyl)-21-methyl-3-oximino-17α-(3-hydroxypropyn-1-yl)-19-norpregna-4,9-diene-3,20-dione;
28. 11β-(4-aminophenyl)-21-methyl-6-fluoro-17α-(1-propynyl)-19-norpregna-4,9-diene-3,20-dione;
29. 11β-(4-aminophenyl)-21-methyl-6-fluoro-17α-(3,3,3-trifluoropropyn-1-yl)-19-norpregna-4,9-diene-3,20-dione;
30. 11β-(4-aminophenyl)-21-methyl-6-fluoro-17α-(3-hydroxypropyn-1-yl)-19-norpregna-4,9-diene-3,20-dione;
31. 11β-(4-aminophenyl)-21-methyl-6-fluoro-3-oximino-17α-(1-propynyl)-19-norpregna-4,9-diene-3,20-dione;
32. 11β-(4-aminophenyl)-21-methyl-6-fluoro-3-oximino-17α-(3,3,3-trifluoropropyn-1-yl)-19-norpregna-4,9-diene-3,20-dione;
33. 11β-(4-aminophenyl)-21-methyl-6-fluoro-3-oximino-17α-(3-hydroxypropyn-1-yl)-19-norpregna-4,9-diene-3,20-dione;
34. 11β-(4-aminophenyl)-6,21-dimethyl-17α-(1-propynyl)-19-norpregna-4,9-diene-3,20-dione;
35. 11β-(4-aminophenyl)-6,21-dimethyl-17α-(3,3,3-trifluoropropyn-1-yl)-19-norpregna-4,9-diene-3,20-dione;
36. 11β-(4-aminophenyl)-6,21-dimethyl-17α-(3-hydroxypropyn-1-yl)-19-norpregna-4,9-diene-3,20-dione;
37. 11β-(4-aminophenyl)-6,21-dimethyl-3-oximino-17α-(1-propynyl)-19-norpregna-4,9-diene-3,20-dione;
38. 11β-(4-aminophenyl)-6,21-dimethyl-3-oximino-17α-(3,3,3-trifluoropropyn-1-yl)-19-norpregna-4,9-diene-3,20-dione;
39. 11β-(4-aminophenyl)-6,21-dimethyl-3-oximino-17α-(3-hydroxypropyn-1-yl)-19-norpregna-4,9-diene-3,20-dione;
40. 11β-(4-aminophenyl)-3-oximino-17α-(1-propynyl)-19-norpregna-4,9-diene-3,20-dione;
41. 11β-(4-aminophenyl)-3-oximino-17α-(3,3,3-trifluoropropyn-1-yl)-19-norpregna-4,9-diene-3,20-dione;
42. 11β-(4-aminophenyl)-3-oximino-17α-(3-hydroxypropyn-1-yl)-19-norpregna-4,9-diene-3,20-dione;
43. 11β-(4-aminophenyl)-6-fluoro-17α-(1-propynyl)-19-norpregna-4,9-diene-3,20-dione;
44. 11β-(4-aminophenyl)-6-fluoro-17α-(3,3,3-trifluoropropyn-1-yl)-19-norpregna-4,9-diene-3,20-dione;
45. 11β-(4-aminophenyl)-6-fluoro-17α-(3-hydroxypropyn-1-yl)-19-norpregna-4,9-diene-3,20-dione;
46. 11β-(4-aminophenyl)-6-fluoro-3-oximino-17α-(1-propynyl)-19-norpregna-4,9-diene-3,20-dione;
47. 11β-(4-aminophenyl)-6-fluoro-3-oximino-17α-(3,3,3-trifluoropropyn-1-yl)-19-norpregna-4,9-diene-3,20-dione;
48. 11β-(4-aminophenyl)-6-fluoro-3-oximino-17α-(3-hydroxypropyn-1-yl)-19-norpregna-4,9-diene-3,20-dione;
49. 11β-(4-aminophenyl)-6-methyl-17α-(1-propynyl)-19-norpregna-4,9-diene-3,20-dione;
50. 11β-(4-aminophenyl)-6-methyl-17α-(3,3,3-trifluoropropyn-1-yl)-19-norpregna-4,9-diene-3,20-dione;
51. 11β-(4-aminophenyl)-6-methyl-17α-(3-hydroxypropyn-1-yl)-19-norpregna-4,9-diene-3,20-dione;
52. 11β-(4-aminophenyl)-6-methyl-3-oximino-17α-(1-propynyl)-19-norpregna-4,9-diene-3,20-dione;
53. 11β-(4-aminophenyl)-6-methyl-3-oximino-17α-(3,3,3-trifluoropropyn-1-yl)-19-norpregna-4,9-diene-3,20-dione;
54. 11β-(4-aminophenyl)-6-methyl-3-oximino-17α-(3-hydroxypropyn-1-yl)-19-norpregna-4,9-diene-3,20-dione;
55. 11β-[4-(N,N-dimethylamino)phenyl]-17α-(1-propynyl)-19-norpregna-4,9-diene-3,20-dione;
56. 11β-[4-(N,N-dimethylamino)phenyl]-17α-(3,3,3-trifluoropropyn-1-yl)-19-norpregna-4,9-diene-3,20-dione;
57. 11β-[4-(N,N-dimethylamino)phenyl]-17α-(3-hydroxypropyn-1-yl)-19-norpregna-4,9-diene-3,20-dione;
58. 11β-[4-(N,N-dimethylamino)phenyl]-21-methoxy-17α-(1-propynyl)-19-norpregna-4,9-diene-3,20-dione;

59. 11β-[4-(N,N-dimethylamino)phenyl]-21-methoxy-17α-(3,3,3-trifluoropropyn-1-yl)-19-norpregna-4,9-diene-3,20-dione;
60. 11β-[4-(N,N-dimethylamino)phenyl]-21-methoxy-17α-(3-hydroxypropyn-1-yl)-19-norpregna-4,9-diene-3,20-dione;
61. 11β-[4-(N,N-dimethylamino)phenyl]-21-methoxy-3-oximino-17α-(1-propynyl)-19-norpregna-4,9-diene-3,20-dione;
62. 11β-[4-(N,N-dimethylamino)phenyl]-21-methoxy-3-oximino-17α-(3,3,3-trifluoropropyn-1-yl)-19-norpregna-4,9-diene-3,20-dione;
63. 11β-[4-(N,N-dimethylamino)phenyl]-21-methoxy-3-oximino-17α-(3-hydroxypropyn-1-yl)-19-norpregna-4,9-diene-3,20-dione;
64. 11β-[4-(N,N-dimethylamino)phenyl]-21-methoxy-6-fluoro-17α-(1-propynyl)-19-norpregna-4,9-diene-3,20-dione;
65. 11β-[4-(N,N-dimethylamino)phenyl]-21-methoxy-6-fluoro-17α-(3,3,3-trifluoropropyn-1-yl)-19-norpregna-4,9-diene-3,20-dione;
66. 11β-[4-(N,N-dimethylamino)phenyl]-21-methoxy-6-fluoro-17α-(3-hydroxypropyn-1-yl)-19-norpregna-4,9-diene-3,20-dione;
67. 11β-[4-(N,N-dimethylamino)phenyl]-21-methoxy-6-fluoro-3-oximino-17α-(1-propynyl)-19-norpregna-4,9-diene-3,20-dione;
68. 11β-[4-(N,N-dimethylamino)phenyl]-21-methoxy-6-fluoro-3-oximino-17α-(3,3,3-trifluoropropyn-1-yl)-19-norpregna-4,9-diene-3,20-dione;
69. 11β-[4-(N,N-dimethylamino)phenyl]-21-methoxy-6-fluoro-3-oximino-17α-(3-hydroxypropyn-1-yl)-19-norpregna-4,9-diene-3,20-dione;
70. 11β-[4-(N,N-dimethylamino)phenyl]-21-methoxy-6-methyl-17α-(1-propynyl)-19-norpregna-4,9-diene-3,20-dione;
71. 11β-[4-(N,N-dimethylamino)phenyl]-21-methoxy-6-methyl-17α-(3,3,3-trifluoropropyn-1-yl)-19-norpregna-4,9-diene-3,20-dione;
72. 11β-[4-(N,N-dimethylamino)phenyl]-21-methoxy-6-methyl-17α-(3-hydroxypropyn-1-yl)-19-norpregna-4,9-diene-3,20-dione;
73. 11β-[4-(N,N-dimethylamino)phenyl]-21-methoxy-6-methyl-3-oximino-17α-(1-propynyl)-19-norpregna-4,9-diene-3,20-dione;
74. 11β-[4-(N,N-dimethylamino)phenyl]-21-methoxy-6-methyl-3-oximino-17α-(3,3,3-trifluoropropyn-1-yl)-19-norpregna-4,9-diene-3,20-dione;
75. 11β-[4-(N,N-dimethylamino)phenyl]-21-methoxy-6-methyl-3-oximino-17α-(3-hydroxypropyn-1-yl)-19-norpregna-4,9-diene-3,20-dione;
76. 11β-[4-(N,N-dimethylamino)phenyl]-21-methyl-17α-(1-propynyl)-19-norpregna-4,9-diene-3,20-dione;
77. 11β-[4-(N,N-dimethylamino)phenyl]-21-methyl-17α-(3,3,3-trifluoropropyn-1-yl)-19-norpregna-4,9-diene-3,20-dione;
78. 11β-[4-(N,N-dimethylamino)phenyl]-21-methyl-17α-(3-hydroxypropyn-1-yl)-19-norpregna-4,9-diene-3,20-dione;
79. 11β-[4-(N,N-dimethylamino)phenyl]-21-methyl-3-oximino-17α-(1-propynyl)-19-norpregna-4,9-diene-3,20-dione;
80. 11β-[4-(N,N-dimethylamino)phenyl]-21-methyl-3-oximino-17α-(3,3,3-trifluoropropyn-1-yl)-19-norpregna-4,9-diene-3,20-dione;
81. 11β-[4-(N,N-dimethylamino)phenyl]-21-methyl-3-oximino-17α-(3-hydroxypropyn-1-yl)-19-norpregna-4,9-diene-3,20-dione;
82. 11β-[4-(N,N-dimethylamino)phenyl]-21-methyl-6-fluoro-17α-(1-propynyl)-19-norpregna-4,9-diene-3,20-dione;
83. 11β-[4-(N,N-dimethylamino)phenyl]-21-methyl-6-fluoro-17α-(3,3,3-trifluoropropyn-1-yl)-19-norpregna-4,9-diene-3,20-dione;
84. 11β-[4-(N,N-dimethylamino)phenyl]-21-methyl-6-fluoro-17α-(3-hydroxypropyn-1-yl)-19-norpregna-4,9-diene-3,20-dione;
85. 11β-[4-(N,N-dimethylamino)phenyl]-21-methyl-6-fluoro-3-oximino-17α-(1-propynyl)-19-norpregna-4,9-diene-3,20-dione;
86. 11β-[4-(N,N-dimethylarnino)phenyl]-21-methyl-6-fluoro-3-oximino-17α-(3,3,3-trifluoropropyn-1-yl)-19-norpregna-4,9-diene-3,20-dione;
87. 11β-[4-(N,N-dimethylamino)phenyl]-21-methyl-6-fluoro-3-oximino-17α-(3-hydroxypropyn-1-yl)-19-norpregna-4,9-diene-3,20-dione;
88. 11β-[4-(N,N-dimethylamino)phenyl]-6,21-dimethyl-17α-(1-propynyl)-19-norpregna-4,9-diene-3,20-dione;
89. 11β-[4-(N,N-dimethylamino)phenyl]-6,21-dimethyl-17α-(3,3,3-trifluoropropyn-1-yl)-19-norpregna-4,9-diene-3,20-dione;
90. 11β-[4-(N,N-dimethylamino)phenyl]-6,21-dimethyl-17α-(3-hydroxypropyn-1-yl)-19-norpregna-4,9-diene-3,20-dione;
91. 11β-[4-(N,N-dimethylamino)phenyl]-6,21-dimethyl-3-oximino-17α-(1-propynyl)-19-norpregna-4,9-diene-3,20-dione;
92. 11β-[4-(N,N-dimethylamino)phenyl]-6,21-dimethyl-3-oximino-17α-(3,3,3-trifluoropropyn-1-yl)-19-norpregna-4,9-diene-3,20-dione;
93. 11β-[4-(N,N-dimethylamino)phenyl]-6,21-dimethyl-3-oximino-17α-(3-hydroxypropyn-1-yl)-19-norpregna-4,9-diene-3,20-dione;
94. 11β-[4-(N,N-dimethylamino)phenyl]-3-oximino-17α-(1-propynyl)-19-norpregna-4,9-diene-3,20-dione;
95. 11β-[4-(N,N-dimethylamino)phenyl]-3-oximino-17α-(3,3,3-trifluoropropyn-1-yl)-19-norpregna-4,9-diene-3,20-dione;
96. 11β-[4-(N,N-dimethylamino)phenyl]-3-oximino-17α-(3-hydroxypropyn-1-yl)-19-norpregna-4,9-diene-3,20-dione;
97. 11β-[4-(N,N-dimethylamino)phenyl]-6-fluoro-17α-(1-propynyl)-19-norpregna-4,9-diene-3,20-dione;
98. 11β-[4-(N,N-dimethylamino)phenyl]-6-fluoro-17α-(3,3,3-trifluoropropyn-1-yl)-19-norpregna-4,9-diene-3,20-dione;
99. 11β-[4-(N,N-dimethylamino)phenyl]-6-fluoro-17α-(3-hydroxypropyn-1-yl)-19-norpregna-4,9-diene-3,20-dione;
100. 11β-[4-(N,N-dimethylamino)phenyl]-6-fluoro-3-oximino-17α-(1-propynyl)-19-norpregna-4,9-diene-3,20-dione;
101. 11β-[4-(N,N-dimethylamino)phenyl]-6-fluoro-3-oximino-17α-(3,3,3-trifluoropropyn-1-yl)-19-norpregna-4,9-diene-3,20-dione;
102. 11β-[4-(N,N-dimethylamino)phenyl]-6-fluoro-3-oximino-17α-(3-hydroxypropyn-1-yl)-19-norpregna-4,9-diene-3,20-dione;

103. 11β-[4-(N,N-dimethylamino)phenyl]-6-methyl-17α-(1-propynyl)-19-norpregna-4,9-diene-3,20-dione;

104. 11β-[4-(N,N-dimethylamino)phenyl]-6-methyl-17α-(3,3,3-trifluoropropyn-1-yl)-19-norpregna-4,9-diene-3,20-dione;

105. 11β-[4-(N,N-dimethylainino)phenyl]-6-methyl-17α-(3-hydroxypropyn-1-yl)-19-norpregna-4,9-diene-3,20-dione;

106. 11β-[4-(N,N-dimethylamino)phenyl]-6-methyl-3-oximino-17α-(1-propynyl)-19-norpregna-4,9-diene-3,20-dione;

107. 11β-[4-(N,N-dimethylamino)phenyl]-6-methyl-3-oximino-17α-(3,3,3-trifluoropropyn-1-yl)-19-norpregna-4,9-diene-3,20-dione;

108. 11β-[4-(N,N-dimethylamino)phenyl]-6-methyl-3-oximino-17α-(3-hydroxypropyn-1-yl)-19-norpregna-4,9-diene-3,20-dione;

109. 11β-[4-(N-methylamino)phenyl]-17α-(1-propynyl)-19-norpregna-4,9-diene-3,20-dione;

110. 11β-[4-(N-methylamino)phenyl]-17α-(3,3,3-trifluoropropyn-1-yl)-19-norpregna-4,9-diene-3,20-dione;

111. 11β-[4-(N-methylamino)phenyl]-17α-(3-hydroxypropyn-1-yl)-19-norpregna-4,9-diene-3,20-dione;

112. 11β-[4-(N-methylamino)phenyl]-21-methoxy-17α-(1-propynyl)-19-norpregna-4,9-diene-3,20-dione;

113. 11β-[4-N-methylamino)phenyl]-21-methoxy-17α-(3,3,3-trifluoropropyn-1-yl)-19-norpregna-4,9-diene-3,20-dione;

114. 11β-[4-(N-methylamino)phenyl]-21-methoxy-17α-(3-hydroxypropyn-1-yl)-19-norpregna-4,9-diene-3,20-dione;

115. 11β-[4-(N-methylamino)phenyl]-21-methoxy-3-oximino-17α-(1-propynyl)-19-norpregna-4,9-diene-3,20-dione;

116. 11β-[4-(N-methylamino)phenyl]-21-methoxy-3-oximino-17α-(3,3,3-trifluoropropyn-1-yl)-19-norpregna-4,9-diene-3,20-dione;

117. 11β-[4-(N-methylamino)phenyl]-21-methoxy-3-oximino-17α-(3-hydroxypropyn-1-yl)-19-norpregna-4,9-diene-3,20-dione;

118. 11β-[4-(N-methylamino)phenyl]-21-methoxy-6-fluoro-17α-(1-propynyl)-19-norpregna-4,9-diene-3,20-dione;

119. 11β-[4-(N-methylamino)phenyl]-21-methoxy-6-fluoro-17α-(3,3,3-trifluoropropyn-1-yl)-19-norpregna-4,9-diene-3,20-dione;

120. 11β-[4-(N-methylamino)phenyl]-21-methoxy-6-fluoro-17α-(3-hydroxypropyn-1-yl)-19-norpregna-4,9-diene-3,20-dione;

121. 11β-[4-(N-methylamino)phenyl]-21-methoxy-6-fluoro-3-oximino-17α-(1-propynyl)-19-norpregna-4,9-diene-3,20-dione;

122. 11β-[4-(N-methylamino)phenyl]-21-methoxy-6-fluoro-3-oximino-17α-(3,3,3-trifluoropropyn-1-yl)-19-norpregna-4,9-diene-3,20-dione;

123. 11β-[4-(N-methylamino)phenyl]-21-methoxy-6-fluoro-3-oximino-17α-(3-hydroxypropyn-1-yl)-19-norpregna-4,9-diene-3,20-dione;

124. 11β-[4-(N-methylamino)phenyl]-21-methoxy-6-methyl-17α-(1-propynyl)-19-norpregna-4,9-diene-3,20-dione;

125. 11β-[4-(N-methylamino)phenyl]-21-methoxy-6-methyl-17α-(3,3,3-trifluoropropyn-1-yl)-19-norpregna-4,9-diene-3,20-dione;

126. 11β-[4-(N-methylamino)phenyl]-21-methoxy-6-methyl-17α-(3-hydroxypropyn-1-yl)-19-norpregna-4,9-diene-3,20-dione;

127. 11β-[4-(N-methylamino)phenyl]-21-methoxy-6-methyl-3-oximino-17α(1-propynyl)-19-norpregna-4,9-diene-3,20-dione;

128. 11β-[4-(N-methylamino)phenyl]-21-methoxy-6-methyl-3-oximino-17α-(3,3,3-trifluoropropyn-1-yl)-19-norpregna-4,9-diene-3,20-dione;

129. 11β-[4-(N-methylamino)phenyl]-21-methoxy-6-methyl-3-oximino-17α-(3-hydroxypropyn-1-yl)-19-norpregna-4,9-diene-3,20-dione;

130. 11β-[4-(N-methylamino)phenyl]-21-methyl-17α-(1-propynyl)-19-norpregna-4,9-diene-3,20-dione;

131. 11β-[4-(N-methylamino)phenyl]-21-methyl-17α-(3,3,3-trifluoropropyn-1-yl)-19-norpregna-4,9-diene-3,20-dione;

132. 11β-[4-(N-methylamino)phenyl]-21-methyl-17α-(3-hydroxypropyn-1-yl)-19-norpregna-4,9-diene-3,20-dione;

133. 11β-[4-(N-methylamino)phenyl]-21-methyl-3-oximino-17α-(1-propynyl)-19-norpregna-4,9-diene-3,20-dione;

134. 11β-[4-(N-methylamino)phenyl]-21-methyl-3-oximino-17α-(3,3,3-trifluoropropyn-1-yl)-19-norpregna-4,9-diene-3,20-dione;

135. 11β-[4-N-methylamino)phenyl]-21-methyl-3-oximino-17α-(3-hydroxypropyn-1-yl)-19-norpregna-4,9-diene-3,20-dione;

136. 11β-[4-N-methylamino)phenyl]-21-methyl-6-fluoro-17α-(1-propynyl)-19-norpregna-4,9-diene-3,20-dione;

137. 11β-[4-N-methylamino)phenyl]-21-methyl-6-fluoro-17α-(3,3,3-trifluoropropyn-1-yl)-19-norpregna-4,9-diene-3,20-dione;

138. 11β-[4-(N-methylamino)phenyl]-21-methyl-6-fluoro-17α-(3-hydroxypropyn-1-yl)-19-norpregna-4,9-diene-3,20-dione;

139. 11β-[4-(N-methylamino)phenyl]-21-methyl-6-fluoro-3-oximino-17α-(1-propynyl)-19-norpregna-4,9-diene-3,20-dione;

140. 11β-[4-(N-methylamino)phenyl]-21-methyl-6-fluoro-3-oximino-17α-(3,3,3-trifluoropropyn-1-yl)-19-norpregna-4,9-diene-3,20-dione;

141. 11β-[4-(N-methylamino)phenyl]-21-methyl-6-fluoro-3-oximino-17α-(3-hydroxypropyn-1-yl)-19-norpregna-4,9-diene-3,20-dione;

142. 11β-[4-(N-methylamino)phenyl]-6,21-dimethyl-17α-(1-propynyl)-19-norpregna-4,9-diene-3,20-dione;

143. 11β-[4-(N-methylamino)phenyl]-6,21-dimethyl-17α-(3,3,3-trifluoropropyn-1-yl)-19-norpregna-4,9-diene-3,20-dione;

144. 11β-[4-(N-methylamino)phenyl]-6,21-dimethyl-17α-(3-hydroxypropyn-1-yl)-19-norpregna-4,9-diene-3,20-dione;

145. 11β-[4-(N-methylamino)phenyl]-6,21-dimethyl-3-oximino-17α-(1-propynyl)-19-norpregna-4,9-diene-3,20-dione;

146. 11β-[4-(N-methylamino)phenyl]-6,21-dimethyl-3-oximino-17α-(3,3,3-trifluoropropyn-1-yl)-19-norpregna-4,9-diene-3,20-dione;

147. 11β-[4-(N-methylamino)phenyl]-6,21-dimethyl-3-oximino-17α-(3-hydroxypropyn-1-yl)-19-norpregna-4,9-diene-3,20-dione;
148. 11β-[4-(N-methylamino)phenyl]-3-oximino-17α-(1-propynyl)-19-norpregna-4,9-diene-3,20-dione;
149. 11β-[4-(N-methylamino)phenyl]-3-oximino-17α-(3,3,3-trifluoropropyn-1-yl)-19-norpregna-4,9-diene-3,20-dione;
150. 11β-[4-(N-methylamino)phenyl]-3-oximino-17α-(3-hydroxypropyn-1-yl)-19-norpregna-4,9-diene-3,20-dione;
151. 11β-[4-(N-methylamino)phenyl]-6-fluoro-17α-(1-propynyl)-19-norpregna-4,9-diene-3,20-dione;
152. 11β-[4-(N-methylamino)phenyl]-6-fluoro-17α-(3,3,3-trifluoropropyn-1-yl)-19-norpregna-4,9-diene-3,20-dione;
153. 11β-[4-(N-methylamino)phenyl]-6-fluoro-17α-(3-hydroxypropyn-1-yl)-19-norpregna-4,9-diene-3,20-dione;
154. 11β-[4-(N-methylamino)phenyl]-6-fluoro-3-oximino-17α-(1-propynyl)-19-norpregna-9-diene-3,20-dione;
155. 11β-[4-(N-methylamino)phenyl]-6-fluoro-3-oximino-17α-(3,3,3-trifluoropropyn-1-yl)-19-norpregna-4,9-diene-3,20-dione;
156. 11β-[4-(N-methylamino)phenyl]-6-fluoro-3-oximino-17α-(3-hydroxypropyn-1-yl)-19-norpregna-4,9-diene-3,20-dione;
157. 11β-[4-(N-methylamino)phenyl]-6-methyl-17α-(1-propynyl)-19-norpregna-4,9-diene-3,20-dione;
158. 11β-[4-(N-methylamino)phenyl]-6-methyl-17α-(3,3,3-trifluoropropyn-1-yl)-19-norpregna-4,9-diene-3,20-dione;
159. 11β-[4-(N-methylamino)phenyl]-6-methyl-17α-(3-hydroxypropyn-1-yl)-19-norpregna-4,9-diene-3,20-dione;
160. 11β-[4-(N-methylamino)phenyl]-6-methyl-3-oximino-17α-(1-propynyl)-19-norpregna-4,9-diene-3,20-dione;
161. 11β-[4-(N-methylamino)phenyl]-6-methyl-3-oximino-17α-(3,3,3-trifluoropropyn-1-yl)-19-norpregna-4,9-diene-3,20-dione;
162. 11β-[4-(N-methylamino)phenyl]-6-methyl-3-oximino-17α-(3-hydroxypropyn-1-yl)-19-norpregna-4,9-diene-3,20-dione;
163. 21-acetoxy-11β-(4-aminophenyl)-17α-(1-propynyl)-19-norpregna-4,9-diene-3,20-dione;
164. 21-acetoxy-11β-(4-aminophenyl)-17α-(3,3,3-trifluoropropyn-1-yl)-19-norpregna-4,9-diene-3,20-dione;
165. 21-acetoxy-11β-(4-aminophenyl)-17α-(3-hydroxypropyn-1-yl)-19-norpregna-4,9-diene-3,20-dione;
166. 21-acetoxy-11β-(4-aminophenyl)-3-oximino-17α-(1-propynyl)-19-norpregna-4,9-diene-3,20-dione;
167. 21-acetoxy-11β-(4-aminophenyl)-3-oximino-17α-(3,3,3-trifluoropropyn-1-yl)-19-norpregna-4,9-diene-3,20-dione;
168. 21-acetoxy-11β-(4-aminophenyl)-3-oximino-17α-(3-hydroxypropyn-1-yl)-19-norpregna-4,9-diene-3,20-dione;
169. 21-acetoxy-11β-(4-aminophenyl)-6-fluoro-17α-(1-propynyl)-19-norpregna-4,9-diene-3,20-dione;
170. 21-acetoxy-11β-(4-aminophenyl)-6-fluoro-17α-(3,3,3-trifluoropropyn-1-yl)-19-norpregna-4,9-diene-3,20-dione;
171. 21-acetoxy-11β-(4-aminophenyl)-6-fluoro-17α-(3-hydroxypropyn-1-yl)-19-norpregna-4,9-diene-3,20-dione;
172. 21-acetoxy-11β-(4-aminophenyl)-6-fluoro-3-oximino-17α-(1-propynyl)-19-norpregna-4,9-diene-3,20-dione;
173. 21-acetoxy-11β-(4-aminophenyl)-6-fluoro-3-oximino-17α-(3,3,3-trifluoropropyn-1-yl)-19-norpregna-4,9-diene-3,20-dione;
174. 21-acetoxy-11β-(4-aminophenyl)-6-fluoro-3-oximino-17α-(3-hydroxypropyn-1-yl)-19-norpregna-4,9-diene-3,20-dione;
175. 21-acetoxy-11β-(4-aminophenyl)-6-methyl-17α-(1-propynyl)-19-norpregna-4,9-diene-3,20-dione;
176. 21-acetoxy-11β-(4-aminophenyl)-6-methyl-17α-(3,3,3-trifluoropropyn-1-yl)-19-norpregna-4,9-diene-3,20-dione;
177. 21-acetoxy-11β-(4-aminophenyl)-6-methyl-17α-(3-hydroxypropyn-1-yl)-19-norpregna-4,9-diene-3,20-dione;
178. 21-acetoxy-11β-(4-aminophenyl)-6-methyl-3-oximino-17α-(1-propynyl)-19-norpregna-4,9-diene-3,20-dione;
179. 21-acetoxy-11β-(4-aminophenyl)-6-methyl-3-oximino-17α-(3,3,3-trifluoropropyn-1-yl)-19-norpregna-4,9-diene-3,20-dione;
180. 21-acetoxy-11β-(4-aminophenyl)-6-methyl-3-oximino-17α-(3-hydroxypropyn-1-yl)-19-norpregna-4,9-diene-3,20-dione;
181. 21-acetoxy-11β-[4-(N,N-dimethylamino)phenyl]-17α-(1-propynyl)-19-norpregna-4,9-diene-3,20-dione;
182. 21-acetoxy-11β-[4-(N,N-dimethylamino)phenyl]-17α-(3,3,3-trifluoropropyn-1-yl)-19-norpregna-4,9-diene-3,20-dione;
183. 21-acetoxy-11β-[4-(N,N-dimethylamino)phenyl]-17α-(3-hydroxypropyn-1-yl)-19-norpregna-4,9-diene-3,20-dione;
184. 21-acetoxy-11β-[4-(N,N-dimethylamino)phenyl]-3-oximino-17α-(1-propynyl)-19-norpregna-4,9-diene-3,20-dione;
185. 21-acetoxy-11β-[4-(N,N-dimethylanino)phenyl]-3-oximino-17α-(3,3,3-trifluoropropyn-1-yl)-19-norpregna-4,9-diene-3,20-dione;
186. 21-acetoxy-11β-[4-(N,N-dimethylamino)phenyl]-3-oximino-17α-(3-hydroxypropyn-1-yl)-19-norpregna-4,9-diene-3,20-dione;
187. 21-acetoxy-11β-[4-(N,N-dimethylamino)phenyl]-6-fluoro-17α-(1-propynyl)-19-norpregna-4,9-diene-3,20-dione;
188. 21-acetoxy-11β-[4-(N,N-dimethylamino)phenyl]-6-fluoro-17α-(3,3,3-trifluoropropyn-1-yl)-19-norpregna-4,9-diene-3,20-dione;
189. 21-acetoxy-11β-[4-(N,N-dimethylamino)phenyl]-6-fluoro-17α-(3-hydroxypropyn-1-yl)-19-norpregna-4,9-diene-3,20-dione;
190. 21-acetoxy-11β-[4-(N,N-dimethylamino)phenyl]-6-fluoro-3-oximino-17α-(1-propynyl)-19-norpregna-4,9-diene-3,20-dione;
191. 21-acetoxy-11β-[4-(N,N-dimethylamino)phenyl]-6-fluoro-3-oximino-17α-(3,3,3-trifluoropropyn-1-yl)-19-norpregna-4,9-diene-3,20-dione;

192. 21-acetoxy-11β-[4-(N,N-dimethylamino)phenyl]-6-fluoro-3-oximino-17α-(3-hydroxypropyn-1-yl)-19-norpregna-4,9-diene-3,20-dione;
193. 21-acetoxy-11β-[4-(N,N-dimethylamino)phenyl]-6-methyl-17α-(1-propynyl)-19-norpregna-4,9-diene-3,20-dione;
194. 21-acetoxy-11β-[4-(N,N-dimethylamino)phenyl]-6-methyl-17α-(3,3,3-trifluoropropyn-1-yl)-19-norpregna-4,9-diene-3,20-dione;
195. 21-acetoxy-11β-[4-(N,N-dimethylamino)phenyl]-6-methyl-17α-(3-hydroxypropyn-1-yl)-19-norpregna-4,9-diene-3,20-dione;
196. 21-acetoxy-11β-[4-(N,N-dimethylamino)phenyl]-6-methyl-3-oximino-17α-(1-propynyl)-19-norpregna-4,9-diene-3,20-dione;
197. 21-acetoxy-11β-[4-(N,N-dimethylamino)phenyl]-6-methyl-3-oximino-17α-(3,3,3-trifluoropropyn-1-yl)-19-norpregna-4,9-diene-3,20-dione;
198. 21-acetoxy-11β-[4-(N,N-dimethylamino)phenyl]-6-methyl-3-oximino-17α-(3-hydroxypropyn-1-yl)-19-norpregna-4,9-diene-3,20-dione;
199. 21-acetoxy-11β-[4-(N-methylamino)phenyl]-17α-(1-propynyl)-19-norpregna-4,9-diene-3,20-dione;
200. 21-acetoxy-11β-[4-(N-methylamino)phenyl]-17α-(3,3,3-trifluoropropyn-1-yl)-19-norpregna-4,9-diene-3,20-dione;
201. 21-acetoxy-11β-[4-(N-methylamino)phenyl]-17α-(3-hydroxypropyn-1-yl)-19-norpregna-4,9-diene-3,20-dione;
202. 21-acetoxy-11β-[4-(N-methylamino)phenyl]-3-oximino-17α-(1-propynyl)-19-norpregna-4,9-diene-3,20-dione;
203. 21-acetoxy-11β-[4-(N-methylamino)phenyl]-3-oximino-17α-(3,3,3-trifluoropropyn-1-yl)-19-norpregna-4,9-diene-3,20-dione;
204. 21-acetoxy-11β-[4-(N-methylamino)phenyl]-3-oximino-17α-(3-hydroxypropyn-1-yl)-19-norpregna-4,9-diene-3,20-dione;
205. 21-acetoxy-11β-[4-(N-methylamino)phenyl]-6-fluoro-17α-(1-propynyl)-19-norpregna-4,9-diene-3,20-dione;
206. 21-acetoxy-11β-[4-(N-methylamino)phenyl]-6-fluoro-17α-(3,3,3-trifluoropropyn-1-yl)-19-norpregna-4,9-diene-3,20-dione;
207. 21-acetoxy-11β-[4-(N-methylamino)phenyl]-6-fluoro-17α-(3-hydroxypropyn-1-yl)-19-norpregna-4,9-diene-3,20-dione;
208. 21-acetoxy-11β-[4-(N-methylamino)phenyl]-6-fluoro-3-oximino-17α-(1-propynyl)-19-norpregna-4,9-diene-3,20-dione;
209. 21-acetoxy-11β-[4-(N-methylamino)phenyl]-6-fluoro-3-oximino-17α-(3-hydroxypropyn-1-yl)-19-norpregna-4,9-diene-3,20-dione;
210. 21-acetoxy-11β-[4-(N-methylamino)phenyl]-6-fluoro-3-oximino-17α-(3,3,3-trifluoropropyn-1-yl)-19-norpregna-4,9-diene-3,20-dione;
211. 21-acetoxy-11β-[4-(N-methylamino)phenyl]-6-methyl-17α-(1-propynyl)-19-norpregna-4,9-diene-3,20-dione;
212. 21-acetoxy-11β-[4-(N-methylamino)phenyl]-6-methyl-17α-(3,3,3-trifluoropropyn-1-yl)-19-norpregna-4,9-diene-3,20-dione;
213. 21-acetoxy-11-[4-(N-methylamino)phenyl]-6-methyl-17α-(3-hydroxypropyn-1-yl)-19-norpregna-4,9-diene-3,20-dione;
214. 21-acetoxy-11β-[4-(N-methylamino)phenyl]-6-methyl-3-oximino-17α-(1-propynyl)-19-norpregna-4,9-diene-3,20-dione;
215. 21-acetoxy-11β-[4-(N-methylamino)phenyl]-6-methyl-3-oximino-17α-(3-hydroxypropyn-1-yl)-19-norpregna-4,9-diene-3,20-dione;
216. 21-acetoxy-11β-[4-(N-methylamino)phenyl]-6-methyl-3-oximino-17α-(3,3,3-trifluoropropyn-1-yl)-19-norpregna-4,9-diene-3,20-dione;

Specific compounds of formula II are 1. 11β-(4-acetylphenyl)-17α-(1-propynyl)-19-norpregna-4,9-diene-3,20-dione;
2. 11β-(4-acetylphenyl)-17α-(3,3,3-trifluoropropyn-1-yl)-19-norpregna-4,9-diene-3,20-dione;
3. 11β-(4-acetylphenyl)-17α-(3-hydroxypropyn-1-yl)-19-norpregna-4,9-diene-3,20-dione;
4. 11β-(4-acetylphenyl)-21-methoxy-17α-(1-propynyl)-19-norpregna-4,9-diene-3,20-dione;
5. 11β-(4-acetylphenyl)-21-methoxy-17α-(3,3,3-trifluoropropyn-1-yl)-19-norpregna-4,9-diene-3,20-dione;
6. 11β-(4-acetylphenyl)-21-methoxy-17α-(3-hydroxypropyn-1-yl)-19-norpregna-4,9-diene-3,20-dione;
7. 11β-(4-acetylphenyl)-21-methyl-17α-(1-propynyl)-19-norpregna-4,9-diene-3,20-dione;
8. 11β-(4-acetylphenyl)-21-methyl-17α-(3,3,3-trifluoropropyn-1-yl)-19-norpregna-4,9-diene-3,20-dione;
9. 11β-(4-acetylphenyl)-21-methyl-17α-(3-hydroxypropyn-1-yl)-19-norpregna-4,9-diene-3,20-dione;
10. 11β-(4-methoxyphenyl)-17α-(1-propynyl)-19-norpregna-4,9-diene-3,20-dione;
11. 11β-(4-methoxyphenyl)-17α-(3,3,3-trifluoropropyn-1-yl)-19-norpregna-4,9-diene-3,20-dione;
12. 11β-(4-methoxyphenyl)-17α-(3-hydroxypropyn-1-yl)-19-norpregna-4,9-diene-3,20-dione;
13. 11β-(4-methoxyphenyl)-21-methoxy-17α-(1-propynyl)-19-norpregna-4,9-diene-3,20-dione;
14. 11β-(4-methoxyphenyl)-21-methoxy-17α-(3,3,3-trifluoropropyn-1-yl)-19-norpregna-4,9-diene-3,20-dione;
15. 11β-(4-methoxyphenyl)-21-methoxy-17α-(3-hydroxypropyn-1-yl)-19-norpregna-4,9-diene-3,20-dione;
16. 11β-(4-methoxyphenyl)-21-methoxy-3-oximino-17α-(1-propynyl)-19-norpregna-4,9-diene-3,20-dione;
17. 11β-(4-methoxyphenyl)-21-methoxy-3-oximino-17α-(3,3,3-trifluoropropyn-1-yl)-19-norpregna-4,9-diene-3,20-dione;
18. 11β-(4-methoxyphenyl)-21-methoxy-3-oximino-17α-(3-hydroxypropyn-1-yl)-19-norpregna-4,9-diene-3,20-dione;
19. 11β-(4-methoxyphenyl)-21-methyl-17α-(1-propynyl)-19-norpregna-4,9-diene-3,20-dione;
20. 11β-(4-methoxyphenyl)-21-methyl-17α-(3,3,3-trifluoropropyn-1-yl)-19-norpregna-4,9-diene-3,20-dione;
21. 11β-(4-methoxyphenyl)-21-methyl-17α-(3-hydroxypropyn-1-yl)-19-norpregna-4,9-diene-3,20-dione;
22. 11β-(4-methoxyphenyl)-21-methyl-3-oximino-17α-(1-propynyl)-19-norpregna-4,9-diene-3,20-dione;

23. 11β-(4-methoxyphenyl)-21-methyl-3-oximino-17α-(3,3,3-trifluoropropyn-1-yl)- 19-norpregna-4,9-diene-3,20-dione;
24. 11β-(4-methoxyphenyl)-21-methyl-3-oximino-17α-(3-hydroxypropyn-1-yl)-19-norpregna-4,9-diene-3,20-dione;
25. 11β-(4-methoxyphenyl)-3-oximino-17α-(1-propynyl)-19-norpregna-4,9-diene-3,20-dione;
26. 11β-(4-methoxyphenyl)-3-oximino-17α-(3,3,3-trifluoropropyn-1-yl)-19-norpregna-4,9-diene-3,20-dione;
27. 11β-(4-methoxyphenyl)-3-oximino-17α-(3-hydroxypropyn-1-yl)-19-norpregna-4,9-diene-3,20-dione;
28. 11β-[4-(methylsulfinyl)phenyl]-17α-(1-propynyl)-19-norpregna-4,9-diene-3,20-dione
29. 11β-[4-(methylsulfinyl)phenyl]-17α-(3,3,3-trifluoropropyn-1-yl)-19-norpregna-4,9-diene-3,20-dione;
30. 11β-[4-(methylsulfinyl)phenyl]-17α-(3-hydroxypropyn-1-yl)-19-norpregna-4,9-diene-3,20-dione;
31. 11β-[4-(methylsulfinyl)phenyl]-21-methoxy-17α-(1-propynyl)-19-norpregna-4,9-diene-3,20-dione;
32. 11β-[4-(methylsulfinyl)phenyl]-21-methoxy-17α-(3,3,3-trifluoropropyn-1-yl)-19-norpregna-4,9-diene-3,20-dione;
33. 11β- [4-(methylsulfinyl)phenyl]-21-methoxy-17α-(3-hydroxypropyn-1-yl)-19-norpregna-4,9-diene-3,20-dione;
34. 11β-[4-(methylsulfinyl)phenyl]-21-methoxy-3-oximino-17α-(1-propynyl)-19-norpregna-4,9-diene-3,20-dione
35. 11β-[4-(methylsulfinyl)phenyl]-21-methoxy-3-oximino-17α-(3,3,3-trifluoropropyn- 1-yl)-19-norpregna-4,9-diene-3,20-dione
36. 11β-[4-(methylsulfinyl)phenyl]-21-methoxy-3-oximino-17α-(3-hydroxypropyn-1-yl)-19-norpregna-4,9-diene-3,20-dione
37. 11β-[4-(methylsulfinyl)phenyl]-21-methyl-17α-(1-propynyl)-19-norpregna-4,9-diene-3,20-dione
38. 11β-[4-(methylsulfinyl)phenyl]-21-methyl-17α-(3,3,3-trifluoropropyn-1-yl)-19-norpregna-4,9-diene-3,20-dione
39. 11β-[4-(methylsulfinyl)phenyl]-21-methyl-17α-(3-hydroxypropyn-1-yl)-19-norpregna-4,9-diene-3,20-dione
40. 11β-[4-(methylsulfinyl)phenyl]-21-methyl-3-oximino-17α-(1-propynyl)-19-norpregna-4,9-diene-3,20-dione
41. 11β-[4-(methylsulfinyl)phenyl]-21-methyl-3-oximino-17α-(3,3,3-trifluoropropyn-1-yl)-19-norpregna-4,9-diene-3,20-dione
42. 11β-[4-(methylsulfinyl)phenyl]-21-methyl-3-oximino-17α-(3-hydroxypropyn-1-yl)-19-norpregna-4,9-diene-3,20-dione
43. 11β-[4-(methylsulfinyl)phenyl]-3-oximino-17α-(1-propynyl)-19-norpregna-4,9-diene-3,20-dione
44. 11β-[4-(methylsulfinyl)phenyl]-3-oximino-17α-(3,3,3-trifluoropropyn-1-yl)-19-norpregna-4,9-diene-3,20-dione
45. 11β-[4-(methylsulfinyl)phenyl]-3-oximino-17α-(3-hydroxypropyn-1-yl)-19-norpregna-4,9-diene-3,20-dione
46. 11β-[4-(methylthio)phenyl]-17α-(1-propynyl)-19-norpregna-4,9-diene-3,20-dione;
47. 11β-[4-(methylthio)phenyl]-17α-(3,3,3-trifluoropropyn-1-yl)-19-norpregna- 4,9-diene-3,20-dione;
48. 11β-[4-(methylthio)phenyl]-17α-(3-hydroxypropyn-1-yl)-19-norpregna-4,9-diene-3,20-dione;
49. 11β-[4-(methylthio)phenyl]-21-methoxy-17α-(1-propynyl)-19-norpregna-4,9-diene-3,20-dione;
50. 11β-[4-(methylthio)phenyl]-21-methoxy-17α-(3,3,3-trifluoropropyn-1-yl)-19-norpregna-4,9-diene-3,20-dione;
51. 11β-[4-(methylthio)phenyl]-21-methoxy-17α-(3-hydroxypropyn-1-yl)-19-norpregna-4,9-diene-3,20-dione;
52. 11β-[4-(methylthio)phenyl]-21-methoxy-3-oximino-17α-(1-propynyl)-19-norpregna-4,9-diene-3,20-dione;
53. 11β-[4-(methylthio)phenyl]-21-methoxy-3-oximino-17α-(3,3,3-trifluoropropyn-1-yl)-19-norpregna-4,9-diene-3,20-dione;
54. 11β-[4-(methylthio)phenyl]-21-methoxy-3-oximino-17α-(3-hydroxypropyn-1-yl)-19-norpregna-4,9-diene-3,20-dione;
55. 11β-[4-(methylthio)phenyl]-21-methyl-17α-(1-propynyl)-19-norpregna-4,9-diene-3,20-dione;
56. 11β-[4-(methylthio)phenyl]-21-methyl-17α-(3,3,3-trifluoropropyn-1-yl)-19-norpregna-4,9-diene-3,20-dione;
57. 11β-[4-(methylthio)phenyl]-21-methyl-17α-(3-hydroxypropyn-1-yl)-19-norpregna-4,9-diene-3,20-dione;
58. 11β-[4-(methylthio)phenyl]-21-methyl-3-oximino-17α-(1-propynyl)-19-norpregna-4,9-diene-3,20-dione;
59. 11β-[4-(methylthio)phenyl]-21-methyl-3-oximino-17α-(3,3,3-trifluoropropyn-1-yl)-19-norpregna-4,9-diene-3,20-dione;
60. 11β-[4-(methylthio)phenyl]-21-methyl-3-oximino-17α-(3-hydroxypropyn-1-yl)-19-norpregna-4,9-diene-3,20-dione;
61. 11β-[4-(methylthio)phenyl]-3-oximino-17α-(1-propynyl)-19-norpregna-4,9-diene-3,20-dione;
62. 11β-[4-(methylthio)phenyl]-3-oximino-17α-(3,3,3-trifluoropropyn-1-yl)-19-norpregna-4,9-diene-3,20-dione;
63. 11β-[4-(methylthio)phenyl]-3-oximino-17α-(3-hydroxypropyn-1-yl)-19-norpregna-4,9-diene-3,20-dione;
64. 21-acetoxy-11β-(4-acetylphenyl)-17α-(1-propynyl)-19-norpregna-4,9-diene-3,20-dione;
65. 21-acetoxy-11β-(4-acetylphenyl)-17α-(3,3,3-trifluoropropyn-1-yl)-19-norpregna-4,9-diene-3,20-dione;
66. 21-acetoxy-11β-(4-acetylphenyl)-17α-(3-hydroxypropyn-1-yl)-19-norpregna-4,9-diene-3,20-dione;
67. 21-acetoxy-11β-(4-methoxyphenyl)-17α-(1-propynyl)-19-norpregna-4,9-diene-3,20-dione;
68. 21-acetoxy-11β-(4-methoxyphenyl)-17α-(3,3,3-trifluoropropyn-1-yl)-19-norpregna-4,9-diene-3,20-dione;
69. 21-acetoxy-11β-(4-methoxyphenyl)-17α-(3-hydroxypropyn-1-yl)-19-norpregna-4,9-diene-3,20-dione;

70. 21-acetoxy-11β-(4-methoxyphenyl)-3-oximino-17α-(1-propynyl)-19-norpregna-4,9-diene-3,20-dione;
71. 21-acetoxy-11β-(4-methoxyphenyl)-3-oximino-17α-(3,3,3-trifluoropropyn-1-yl)-19-norpregna-4,9-diene-3,20-dione;
72. 21-acetoxy-11β-(4-methoxyphenyl)-3-oximino-17α-(3-hydroxypropyn-1-yl)-19-norpregna-4,9-diene-3,20-dione;
73. 21-acetoxy-11β-[4-(methylsulfinyl)phenyl]-17α-(1-propynyl)-19-norpregna-4,9-diene-3,20-dione
74. 21-acetoxy-11β-[4-(methylsulfinyl)phenyl]-17α-(3,3,3-trifluoropropyn-1-yl)-19-norpregna-4,9-diene-3,20-dione
75. 21-acetoxy-11β-[4-(methylsulfinyl)phenyl]-17α-(3-hydroxypropyn-1-yl)-19-norpregna-4,9-diene-3,20-dione
76. 21-acetoxy-11β-[4-(methylsulfinyl)phenyl]-3-oximino-17α-(1-propynyl)-19-norpregna-4,9-diene-3,20-dione
77. 21-acetoxy-11β-[4-(methylsulfinyl)phenyl]-3-oximino-17α-(3,3,3-trifluoropropyn-1-yl)-19-norpregna-4,9-diene-3,20-dione
78. 21-acetoxy-11β-[4-(methylsulfinyl)phenyl]-3-oximino-17α-(3-hydroxypropyn-1-yl)-19-norpregna-4,9-diene-3,20-dione
79. 21-acetoxy-11β-[4-(methylthio)phenyl]-17α-(1-propynyl)-19-norpregna-4,9-diene-3,20-dione;
80. 21-acetoxy-11β-[4-(methylthio)phenyl]-17α-(3,3,3-trifluoropropyn-1-yl)-19-norpregna-4,9-diene-3,20-dione;
81. 21-acetoxy-11β-[4-(methylthio)phenyl]-17α-(3-hydroxypropyn-1-yl)-19-norpregna-4,9-diene-3,20-dione;
82. 21-acetoxy-11β-[4-(methylthio)phenyl]-3-oximino-17α-(1-propynyl)-19-norpregna-4,9-diene-3,20-dione;
83. 21-acetoxy-11β-[4-(methylthio)phenyl]-3-oximino-17α-(3,3,3-trifluoropropyn-1-yl)-19-norpregna-4,9-diene-3,20-dione;
84. 21-acetoxy-11β-[4-(methylthio)phenyl]-3-oximino-17α-(3-hydroxypropyn-1-yl)-19-norpregna-4,9-diene-3,20-dione;

Compounds of the invention may be synthesized by conventional methods known to those of ordinary skill in the art, such as the scheme shown in Chart 1, beginning with estrone, which is converted to its methyl ether (2) in quantitative yield by reaction with $K_2CO_3$ and MeI in MeOH. The methyl ether of estrone is then converted to the corresponding 17-cyano compound (3) by reaction of the ketone with t-BuOK and TosMIC in DME (Oldenziel, O. H. and van Leusen, A. M. *Tetrahedron Lett.*, 13, 1357–1360 (1973); Bull, J. R. and Tuinman, A. *Tetrahedron*, 31, 2151–2155 (1975). The 17-carbonitrile is obtained in 76% yield as a mixture of 17α and 17β isomers. By use of MeMgBr in refluxing THF, the 17-carbonitrile is converted to the corresponding 17-acetyl compound (4) in quantitative yield (cf. Bull and Tuinman, 1975). Refluxing 4 in toluene with acetic anhydride and p-TsOH gives enol acetate 5 as a mixture of E and Z isomers in 70% yield.

The enol acetate is converted to the 17β-acetyl-17α-hydroxymethyl compound (6) in 65% yield by use of freshly fused $ZnCl_2$ and gaseous formaldehyde in dry ether [cf. J. R. Reel and C. E. Cook, U.S. Pat. No. 4,512,986 (1985)].

The 20-ketone is reduced to a corresponding mixture of 20-alcohol epimers in 90% yield by lithium aluminum hydride (LAH) in dry tetrahydrofuran (THF). These need not be separated, and the mixture can be carried on through the next three steps in the synthetic scheme without purification of the intermediates. Birch reduction with lithium and liquid $NH_3$ in THF and t-BuOH gives the enol ether 8, which is treated with oxalic acid to afford the 5(10)-en-3-one (9). Treatment of this compound with pyridinium tribromide in dry pyridine oxidizes it to the desired 4,9-dien-3-one (10) in an overall 3-step yield of 55–60% after purification.

Oxidation of the two alcohol functions to ketone and aldehyde is achieved by reaction of 10 under Swern conditions to give the desired 17β-acetyl-17α-formyl compound (11) in 70–75% yield after purification. The aldehyde reacts (cf. Reel and Cook, 1985) with the Seyferth/Gilbert reagent (Brown, D. G.; Velthuisen, E. J.; Commenford, J. R.; Brisbois, R. G.; and Hoye, T. R. *J. Org. Chem.*, 61, 2540–2541 (1996)) to afford the 17β-acetyl-17α-ethynyl compound (12) in 78% yield.

Monoketalization of 12 is achieved in 80% yield by treating the diketone in benzene with ethylene glycol and a catalytic amount of p-TsOH to yield the 3-ketal-5(10),9(11)-dien-20-one derivative (13). Reduction of the 20-ketone with $NaBH_4$ and treatment of the resulting alcohol 14 in dry pyridine with trimethylsilyl chloride (TMSCl) produces the TMS ether 15 in 80% yield. Treatment of this compound with lithium N-tert-butyl-N-trimethylsilylamide and methyl iodide leads to the propynyl compound (16) in 80–90% yield.

Formation of the 5(10)α-epoxide 17 is readily achieved by treating 16 with hexafluoroacetone, $H_2O_2$, and $Na_2HPO_4$ in $CH_2Cl_2$ at 0° C. overnight. This reaction results both the α and the β epoxides, but upon purification the α-epoxide is isolated in about 60% yield and 90% purity. Reaction of the epoxide with the aryl Grignard reagent from p-N,N-dimethylaminophenyl bromide and CuCl results in aryl compound 18a in isolated yields of 70–75%.

Deketalization at the 3 position, dehydration of the C5 hydroxyl, and deprotection of the 20-hydroxy dienone are achieved in a single step by treatment of compound 18a with aqueous trifluoroacetic acid in $CH_2Cl_2$. Upon purification the desired 20-hydroxy compound 19a is obtained in yields up to 90%. Oxidation to the 20-ketone A-1 is then achieved by treatment with o-iodoxybenzoic acid (IBX) (cf. Frigerio, M. and Santagostino, M. *Tetrahedron Lett.*, 35(43), 8019–8022 (1994)), although it has been reported that IBX does not work in the presence of anilines (Frigerio, M.; Santagostino, M.; Sputore, S.; and Palmisano, G. *J. Org. Chem.*, 60, 7272–7276 (1995)). Use of a large excess of the IBX results in the desired product (A-1) together with 10–20% of the corresponding N-formyl compound formed by oxidation of one of the methyl groups of the N,N-dimethylaminophenyl moiety to formyl. By use of dimethylsulfoxide (DMSO) as the sole solvent and only 1.52 equivalents of IBX, A-1 is obtained in 43–51 % yield with 20–25% recovery of starting alcohol (19a), which can be recycled to increase the overall yield.

The synthesis of other 17α-propynyl compounds may be achieved by analogous procedures (see Examples).

Steroids having progestational, antiprogestational and/or antiglucocorticoid activity have use in the control of fertility in humans and non-human mammals such as primates, domestic pets and farm animals, and in the treatment of medical conditions in animals or humans in which these activities are beneficial. Thus they may be useful in the treatment of conditions such as fibroids, Cushing's syndrome, glaucoma, endometriosis, cervical ripening prior to delivery, hormone replacement therapy, premenstrual syndrome and cancer in addition to their use in the control of fertility and reproduction.

The compounds of the present invention may be administered by a variety of methods. Thus, those products of the invention that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration may be administered by depot injection, implants including Silastic™ and biodegradable implants, intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives.

Suitable dispersing or wetting agents and suspending agents are exemplified by those disclosed above. Additional excipients, for example sweetening, flavoring and coloring agents, may also be present.

The pharmaceutical composition of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as by aseptic filtration, irradiation or terminal sterilization (e.g. autoclaving).

Aqueous formulations (i.e oil-in-water emulsions, syrups, elixers and injectable preparations) may be formulated to achieve the pH of optimum stability. The determination of the optimum pH may be performed by conventional methods known to those of ordinary skill in the art. Suitable buffers may also be used to maintain the pH of the formulation.

The compounds of this invention may also be administered in the form of suppositories for rectal administration of the drug. These compositions can be prepared by mixing the drug with a suitable nonirritating excipient which is solid at ordinary temperatures but liquid at the rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

Products of the invention which are preferably administered by the topical route may be administered as applicator sticks, solutions, suspensions, emulsions, gels, creams, ointments, pastes, jellies, paints, powders, and aerosols.

Products having anti-glucocorticoid activity are of particular value in pathological conditions characterized by excess endogenous glucocorticoid such as Cushing's syndrome, hirsutism and in particular when associated with the adrenogenital syndrome, ocular conditions associated with glucocorticoid excess such as glaucoma, stress symptoms associated with excess glucocorticoid secretion and the like.

Products having progestational activity are of particular value as progestational agents, ovulation inhibitors, menses regulators, contraceptive agents, agents for synchronization of fertile periods in cattle, and the like. When used for contraceptive purposes, they may conveniently be admixed with estrogenic agents, such as for example as ethynylestradiol or estradiol esters.

Products having anti-progestational activity are characterized by antagonizing the effects of progesterone. As such, they are of value in assisting in labor and delivery, in treatment of fibroids and endometriosis and in hormone replacement therapy.

The compounds of the invention may be used for control of fertility during the whole of the reproductive cycle. They are of particular value as postcoital contraceptives, for rendering the uterus inimical to implantation, and as "once a month" contraceptive agents. They may be used in conjunction with prostaglandins, oxytocics, estrogens and the like.

A further important utility for the products of the invention lies in their ability to slow down growth of hormone-dependent cancers. Such cancers include kidney, breast, endometrial, ovarian cancers, and prostate cancer which are characterized by possessing progesterone receptors and may be expected to respond to the products of this invention. Other utilities of anti-progestational agents include treatment of fibrocystic disease of the breast. Certain cancers and in particular melanomas may respond favorably to corticoid/anticorticoid therapy.

The compounds according to the present invention may be administered to any warm-blooded mammal such as humans, domestic pets, and farm animals. Domestic pets include dogs, cats, etc. Farm animals include cows, horses, pigs, sheep, goats, etc.

The amount of active ingredient that may be combined with a carrier material to produce a single dosage form will vary depending upon the disease treated, the mammalian species, and the particular mode of administration. A therapeutically effective amount may be determined by routine experimentation and by analogy from the amounts used to treat the same disease states with analogous steroid compounds For example, a unit dose of the steroid may preferably contain between 0.1 milligram and 1 gram of the active ingredient. A more preferred unit dose is between 0.001 and 0.5 grams. For the specific treatment of endometriosis or fibroids an amount of 0.01 to 10 mg/kg of body weight, preferably from 0.1 to 3 mg/kg may be administered. Similar dosages may be used for the other therapeutic purposes of these compounds. Ordinarily the compounds may be administered daily 1 to 4 times per day, preferably 1 to 2 times per day, but for uses such as for example in hormone replacement therapy, they may be administered in a cyclophasic regimen. In any case the frequency and timing of dosage will depend upon factors such as the half-life of the specific compound in the body, the dosage formulation and the route of administration. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the art.

Such compounds are useful in the treatment of endometriosis, uterine leiomyomas (fibroids) and certain cancers and tumors, in hormone replacement therapy as well as in the control of various steps in reproduction and fertility, such as contraception. A more detailed description of the potential uses of such compounds is given in Donaldson, Molly S.; Dorflinger, L.; Brown, Sarah S.; Benet, Leslie Z., Editors, *Clinical Applications of Mifepristone (RU 486) and Other Antiprogestins*, Committee on Antiprogestins: Assessing the Science, Institute of Medicine, National Academy Press, 1993. They are also useful as intermediates for the synthesis of other steroids.

Synthetic Procedures

Having generally described this invention, a further understanding can be obtained by reference to certain specific examples which are provided herein for purposes of illustration only and are not intended to be limiting unless otherwise specified. The compounds of the present invention may be prepared by conventional methods known to those of ordinary skill in the art without undue experimentation.

EXAMPLES

General Methods.

Unless otherwise stated, reagent-grade chemicals were obtained from commercial sources and were used without further purification. Ether and tetrahydrofuran (THF) were freshly distilled from sodium benzophenone ketyl pair under nitrogen. All moisture- and air-sensitive reactions and reagent transfers were carried out under dry nitrogen or argon. Thin layer chromatography (TLC) was performed on EM Science precoated silica gel 60 F254 plates. Compounds were normally visualized by UV light (254 nm) or para-anisaldehyde spray. Preparative column chromatography employed EM Science silica gel, 60 Å (230–400 mesh). Solutions were concentrated by use of a rotoevaporator under water aspirator pressure at ambient temperature. Melting points were taken on a Mel-Temp II and are uncorrected. Unless otherwise noted, $^1$H NMR spectra were obtained at 250 MHz on a Bruker AC 250 spectrometer in $CDCl_3$ as solvent with tetramethylsilane (TMS) as internal standard. Chemical shifts are reported in units of ppm downfield from TMS. Mass spectra were normally obtained by electron impact at 70 eV on a Hewlett Packard 5989A instrument. Elemental analyses were performed by Atlantic Microlab Inc., Atlanta, Ga.

Example 1

Synthesis of 11β-[4-(N,N-Dimethylamino)phenyl]-17α-(1-propynyl)-19-norpregna-4,9-diene-3,20-dione (A-1).

3-Methoxyestra-1,3,5(10)-trien-17-one (2)

Estrone (1), 100.0 g, 370 mmol) was dissolved in MeOH (1.5 L), followed by the addition of $K_2CO_3$ (300.0 g, 2.17 mol). MeI (310 mL, 4.98 mol) was added and the mixture stirred at room temperature for 70 h. The reaction mixture was concentrated in vacuo to remove some of the MeOH and was then poured into ice water, forming a precipitate. The solid was collected by partitioning into $CH_2Cl_2$. The organic layer was dried over $MgSO_4$, and the solvent was removed in vacuo to yield compound 2 (105.0 g) as white crystals in quantitative yield. $^1$H NMR δ 0.91 (s, 3, C-18 H), 3.78 (s, 3, MeO), 6.65 (s, 1, C-4 H), 6.72 (d, 1, J=8.6 Hz, C-2 H), 7.21 (d, 1, J=8.6 Hz, C-1 H).

17-Cyano-3-methoxyestra-1,3,5(10)-triene (3).

Compound 2 (50.0 g, 176.0 mmol) was dissolved in dimethoxyethane (DME, 1.2 L) under an inert atmosphere. t-BuOH (170 mL) was added followed by the addition of t-BuOK (197.0 g, 1.76 mol) in DME (50 mL). p-Toluenesulfonyl isocyanate (TosMIC, 68.7 g, 352.0 mmol) in DME (600 mL) and t-BuOH (50 mL) was added slowly over 1.5 h. The reaction was quenched after 1.3 h with saturated $NH_4Cl$ (2 L). After being stirred for several hours, the reaction mixture was extracted with $CH_2Cl_2$. The organic layers were combined and washed with brine, dried over $MgSO_4$, and the solvent was removed in vacuo, yielding a brown oily solid. Purification by flash column chromatography ($SiO_2$; 3:1 EtOAc/hexanes increasing to 5:1 EtOAc/hexanes) afforded compound 3 (39.8 g) as a mixture of 17α/β isomers in 76% yield. $^1$H NMR δ 0.86 (s, 3, C-18 H, major), 0.96 (s, 3, C-18 H, minor), 3.78 (s, 3, MeO), 6.64 (s, 1, C-4 H), 6.71 (d, 1, J=8.5 Hz, C-2 H), 7.21 (d, 1, J=8.7Hz, C-1H).

3-Methoxy-19-norpregna-1,3,5(10)-trien-20-one (4).

Compound 3 (73.0 g, 247 mmol) was dissolved in dry THF (800 mL) under an inert atmosphere. MeMgBr in THF (800 mL, 1.12 mol) was added and the reaction mixture heated to reflux for 3.5 h, then cooled to room temperature. The reaction was quenched with cold saturated $NH_4Cl$ and then acidified with HCl. The reaction mixture was extracted with $CH_2Cl_2$ (2×300 mL). The organic layers were combined and washed with brine, dried over $MgSO_4$ and concentrated in vacuo to yield compound 4 (77.0 g) as a pale yellow solid in quantitative yield. The product was a mixture of 17α/β isomers, and no further purification was performed. $^1$H NMR δ 0.65 (s, 3, C-18 H, major), 0.94 (s, 3, C-18 H, minor), 2.16 (s, 3, C-21 H), 3.78 (s, 3, MeO), 6.63 (d, 1, J=2.7 Hz, C-4 H), 6.71 (dd, 1, J=8.6, 2.8 Hz, C-2 H), 7.21 (d, 1, J=8.7 Hz, C-1 H).

20-Acetoxy-3-methoxy-19-norpregna-1,3,5(10),17(20)-tetraene (5).

Crude compound 4 (56.0 g, 179.0 mmol) was dissolved in toluene (900 mL), followed by the addition of $Ac_2O$ (300 mL, 3.17 mol) and p-TsOH (5.0 g, 45 mmol). The mixture was heated to reflux and 500 mL of tolune was distilled off. The reaction mixture was cooled and more $Ac_2O$ (210 mL, 2.22 mol) and p-TsOH (5.0 g, 45 mmol) were added. The reaction mixture was then heated at reflux overnight. The reaction mixture was cooled to room temperature and quenched with an ice cold mixture of NaOH and $NaHCO_3$ until the reaction mixture was no longer acidic. The aqueous and organic layers were separated. The aqueous layer was extracted with $CH_2Cl_2$. The organic layers were combined, washed with brine, and dried over $MgSO_4$. The solvent was removed in vacuo to yield a brown oily solid. Purification by flash column chromatography ($SiO_2$; 4:1 $CH_2Cl_2$/hexanes) afforded compound 5 (44.5 g) as a mixture of E/Z isomers in 70% yield. $^1$H NMR δ 0.87 (s, 3, C-18 H, major), 0.92 (s, 3, C-18 H, minor), 2.11 (s, 3, C-21 H, minor), 2.14 (s, 3, C-21 H, major), 3.77 (s ,3, MeO), 6.63 (s, 1H, C-4 H), 6.71 (d, 1, J=8.4 Hz, C-2 H), 7.21 (d, 1, J=8.5 Hz, C-1 H).

17α-Hydroxymethyl-3-methoxypregna-1,3,5(10)-trien-20-one (6).

Compound 5 (49.0 g, 138.4 mmol) was dissolved in dry ether (1.3 L) under an inert atmosphere and cooled to 0° C. MeLi (252 mL, 352.8 mmol) was added slowly over 5 min and stirred at 0° C. for 20 min followed by the addition of freshly fused $ZnCl_2$ (39.0 g, 286.1 mmol) in dry ether (250 mL). After an additional 20 min stirring at 0° C., paraformaldehyde (20.0 g, 605 mmol) was heated and bubbled into the reaction mixture, turning it a cloudy cream color. The reaction mixture was warmed to room temperature, quenched with $NH_4Cl$ and extracted with $CH_2Cl_2$. The organic layers were combined, washed with brine and dried over $MgSO_4$. The solvent was removed in vacuo to yield a yellow solid. Purification by flash column chromatography (pure $CH_2Cl_2$ increased to 5% acetone) afforded 6 (32.4 g) as a white solid in 68% yield. $^1$H NMR δ 7.18 (d, 1, J=8.5 Hz, C-1 H), 6.70 (d, 1, J=8.6 Hz, C-2 H), 6.63 (s, 1, C-4 H), 4.24 (dd, 1, J=4.2, 10.2 Hz, $CH_2OH$), 3.77 (s, 3, MeO), 3.64 (dd, 1, J=3.7, 10.4 Hz, $CH_2OH$), 2.26 (s, 3, C-21 H), 0.71 (s, 3, C-18 H).

17α-Hydroxymethyl-3-methoxy-19-norpregna-1,3,5(10)-trien-20-ol (7).

Compound 6 (12.0 g, 35.0 mmol) was dissolved in dry THF (300 mL) under an inert atmosphere and cooled to 0° C. LAH (2.7 g, 71.1 mmol) was added portionwise over 10 min. The reaction mixture was stirred at 0° C. for 1.5 h and then slowly quenched with a saturated solution of Rochelle's salt (60 mL). The organic and aqueous layers were separated. The aqueous layer was extracted with ether (5×75 mL). The organic layers were combined and dried over $MgSO_4$. The solvent was removed in vacuo to yield a white solid as a mixture of C-20 epimers. Purification by flash column chromatography ($SiO_2$; $CH_2Cl_2$ pure up to 10% acetone) afforded three fractions [pure less polar isomer (3.7 g, 31%), mixture of less and more polar isomers (3.45 g, 26%), and pure more polar isomer (3.85 g, 32%)] to give compound 7 in an overall yield of 89%. $^1$H NMR (less polar isomer) δ 1.01 (s, 3, C-18 H), 1.34 (d, 3, J=6.5 Hz, C-21 H), 3.78 (s, 3, MeO), 6.62 (dd, 1, J=2.7 Hz, C-4 H), 6.75 (d, 1, J=2.75, 8.6 Hz, C-2 H), 7.21 (d, 1, J=8.53 Hz, C-1 H).

17α-Hydroxymethyl-3-methoxy-19-norpregna-2,5(10)-dien-20-ol (8) (less polar isomer).

Liquid $NH_3$ (250 mL) was condensed at −78° C. under an inert atmosphere. Compound 7 (pure less polar isomer; 2.75 g, 7.98 mmol) in THF (150 mL) and t-BuOH (30 mL) was added slowly over 20 min, followed by the addition of the lithium wire (1.0 g, 144.0 mmol). The reaction mixture turned blue and was stirred for 2 h at −78° C. The residue was slowly quenched with MeOH (30 mL) and warrned to room temperature to evaporate the $NH_3$. The reaction mixture was partitioned with unsaturated $NH_4Cl$ and the aqueous layer extracted with EtOAc. The organic layers were combined, washed with $NH_4Cl$ and brine, and dried over $Na_2SO_4$. The solvent was removed in vacuo to yield compound 8 as a white solid. This was used immediately without further purification.

20-Hydroxy-17α-hydroxymethyl-19-norpregn-5(10)-en-3-one (9, less polar isomer).

Crude compound 8 (assumed 7.98 mmol) was dissolved in a mixture of THF and dioxane followed by the addition of oxalic acid (1.8 g, 20.0 mmol) in water (50 mL). The mixture was stirred at room temperature overnight and slowly quenched with dilute $NaHCO_3$. The aqueous layer was extracted with $CH_2Cl_2$. The organic layers were combined, washed with $NH_4Cl$, $H_2O$, and brine, and dried over $Na_2SO_4$. The solvent was removed in vacuo to yield compound 9 as a white solid. This was used without any further purification.

20-Hydroxy-17α-hydroxymethyl-19-norpregna-4,9-dien-3-one (10) (less polar isomer).

Crude compound 9 (assumed 7.98 mmol) was dissolved in dry pyridine (75 mL) under an inert atmosphere and cooled to 0° C. Pyridinium tribromide (3.11 g, 9.72 mmol) was added, turning the reaction mixture orange. The reaction mixture was allowed to slowly warm to room temperature overnight. The reaction was quenched with 5% $Na_2SO_3$ (100 mL) and the mixture extracted three times with CH$_2$Cl$_2$. The organic layers were combined and washed with dilute HCl, dilute CuSO$_4$, H$_2$O, and brine. This was dried over Na$_2$SO$_4$ and the solvent removed in vacuo to yield a brown solid. Purification by flash column chromatography (SiO$_2$; 1:1 EtOAc/hexanes up to 3:2 EtOAc/hexanes) afforded compound 10 (1.38 g) as a white solid in an overall yield of 53% for the 3 steps.

17α-Hydroxymethyl-3-methoxy-19-norpregna-2,5(10)-dien-20-ol (8) (Isomer mixture).

Liquid NH$_3$ (1.5 L) was condensed at −78° C. under an inert atmosphere. Compound 7 (mixture of isomers; 39.0 g, 113.2 mmol) in THF (1.1 L) and t-BuOH (400 mL) was added slowly over 50 min, followed by the addition of lithium wire (8.3 g, 1.195 mol). The blue reaction mixture was stirred for 3 h at −78° C. The reaction was slowly quenched with MeOH (250 mL) and warmed to room temperature to evaporate the NH$_3$ overnight. The reaction mixture was partitioned with aqueous NH$_4$Cl and the aqueous layer extracted with EtOAc (3×500 mL). The organic layers were combined, washed with H$_2$O and brine, and dried over MgSO$_4$. The solvent was removed in vacuo to give compound 8 as a white solid in a quantitative crude yield. This was used immediately without further purification.

20-Hydroxy-17α-hydroxymethyl-19-norpregn-5(10)-en-3-one (9) (Isomer mixture).

Crude compound 8 (assumed 113.2 mmol) was dissolved in a mixture of THF (650 mL) and dioxane (800 mL) followed by the addition of oxalic acid (22.5 g, 250.0 mmol) in water (500 mL). The reaction mixture was stirred at room temperature overnight and slowly quenched with dilute NaHCO$_3$. The aqueous layer was extracted three times with CH$_2$Cl$_2$. The organic layers were combined, washed with saturated NaHCO$_3$ and brine, and dried over MgSO$_4$. The solvent was removed in vacuo to yield compound 9 as a white solid. Purification by flash column chromatography (1:1 EtOAc/hexanes) afforded 9 (35.7 g) as a while solid in 95% yield for the two steps.

20-Hydroxy-17α-hydroxymethyl-19-norpregna-4,9-dien-3-one (10) (Isomer mixture).

Crude compound 9 (35.5 g, 106.7 mmol) was dissolved in dry pyridine (600 mL) under an inert atmosphere and cooled to −20° C. Pyridinium tribromide (41.7 g, 117.3 mmol) was added and the reaction mixture was allowed to warm slowly to room temperature overnight. The reaction was quenched with Na$_2$SO$_3$. The majority of the solvent was removed in vacuo. The slurry remaining was diluted with water and extracted three times with CH$_2$Cl$_2$. The organic layers were combined and washed with H$_2$O, dilute CuSO$_4$, H$_2$0, and brine, dried over Na$_2$SO$_4$ and the solvent removed in vacuo to yield an orange solid. Purification by flash column chromatography (1:1 EtOAc/hexanes up to 2:1 EtOAc/hexanes) afforded compound 10 (22.32 g, 63% yield) as a white solid. $^1$H NMR (less polar isomer)δ 1.14 (s, 3, C-18 H), 1.33 (d, 3, J=6.47 Hz, C-21 H), 3.74 (d, 1, J=9.2 Hz), 3.3, 8.0 Hz), 5.67 (s, 1, C-4 H); (more polar isomer) δ 0.93 (s, 3, C-18 H), 1.35 (d, 3, J=6.42 Hz, C-21 H), 3.52 (t, 1, J=3.52 Hz), 5.67 (s, 1, C-4 H).

17α-Formyl-19-norpregna-4,9-diene-3,20-dione (11).

Oxalyl chloride (31.8 mL, 63.6 mmol) in CH$_2$Cl$_2$ (10 mL) was cooled under an inert atmosphere to 60° C. Dimethylsulfoxide (DMSO, 6.0 mL, 84.6 mmol) was added dropwise; gas evolution was observed. The reaction mixture was stirred for 30 min followed by the slow addition of compound 10 (7.0 g, 21.2 mmol; mixture of isomers) in dry CH$_2$Cl$_2$ (44 mL). The reaction mixture was stirred for 30 min at 60° C. Et$_3$N (19.5 mL, 140.0 mmol) was then added and the mixture stirred for 20 min at 60° C. and then slowly warmed to room temperature over 1 h. The reaction was quenched with H$_2$O, extracted three times with CH$_2$Cl$_2$, and washed with H$_2$O and brine. The organic layer was dried over MgSO$_4$, and the solvent removed in vacuo to yield a brown oily solid. The product was used directly in the next step. $^1$H NMR δ 9.84 (s, 1, formyl H), 5.68 (s, 1, C-4 H), 2.34 (s, 3, C-21 H), 0.96 (s, 3, C-18 H).

17α-Ethynyl-19-norpregna-4,9-diene-3,20-dione (12).

t-BuOK (3.08 g, 25.2 mmol) in dry THF (50 mL) and (CH$_3$O)$_2$POCHN$_2$ (3.78 g, 25.18 mmol; Seyferth/Gilbert reagent) in dry THF (25 mL) were cooled separately under an inert atmosphere to −78° C. The Seyferth/Gilbert reagent was then treated slowly with the t-BuOK solution and stirred for 10 min at −78° C. Compound 11 from the above reaction (assumed 19.0 mmol) in dry THF (80 mL) was added slowly. The reaction mixture was stirred at −78° C. and slowly warmed to room temperature overnight. The reaction was quenched with H$_2$O and extracted four times with CH$_2$Cl$_2$. The organic layers were combined, washed with brine, and dried over MgSO$_4$. The solvent was removed in vacuo to leave a brown solid. Purification by flash column chromatography (1:1 EtOAc/hexanes) produced the desired product 12 as a pale yellow solid (4.98 g) in 73% overall yield from 10. $^1$H NMR δ 5.70 (s, 1, C-4 H), 2.45 (s, 1, ethynyl H), 2.32 (s, 3, C-21 H), 0.76 (s, 3, c-18 H).

3,3-[1,2-Ethanediylbis(oxy)]-17α-ethynyl-19-norpregna-5(10),9(1 I)-dien-20-one (13).

Compound 12 (5.67 g, 17.6 mmol) was dissolved in benzene (300 mL) and treated with ethylene glycol (11.8 mL, 211.8 mmol) and p-TsOH (330 mg, 1.74 mmol). The reaction mixture was heated to reflux for 1.5 h, cooled to room temperature and quenched with aqueous NaHCO$_3$. The aqueous layer was extracted twice with EtOAc. The organic layers were combined, washed with H$_2$O and brine, and dried over MgSO$_4$. The solvent was removed in vacuo to leave a yellow solid. Purification by means of flash column chromatography (1:1 EtOAc/hexanes) afforded the desired product 13 (6.11 g, 95% yield). $^1$H NMR δ 5.60 (br s, 1, C-11 H), 4.04 (s, 4, ketal), 2.43 (s, 1, ethynyl H), 2.31 (s, 3, C-21 H), 0.59 (s, 3, C-18 H).

3,3-[1,2-Ethanediylbis(oxy)]-17α-ethynyl-19-norpregna-5(10),9(11)-dien-20-ol (14).

Compound 13 (6.1 g, 16.6 mmol) was dissolved in dry THF (90 mL) and EtOH (50 mL) under an inert atmosphere. NaBH$_4$ (1.26 g, 33.3 mmol) was added and the reaction mixture warmed for 8 h. The reaction was quenched with aqueous NH$_2$OH.HCl (adjusted to a pH of 7). The reaction mixture was extracted three times with CH$_2$Cl$_2$. The organic layers were combined, washed with brine and dried over Na$_2$SO$_4$. The solvent was removed in vacuo to give a white solid. The crude yield was quantitative and the material was used without further purification in the next step. $^1$H NMR δ 5.59 (br s, 1, C-I1 H), 3.99 (s, 4, ketal), 3.94 (m, 1, C-20 H), 2.29 (s, 1, ethynyl H), 1.27 (d, 3, J=6.2 Hz, C-21 H), 0.82 (s, 3, C-18 H).

3,3-[1,2-Ethanediylbis(oxy)]-17α-ethynyl-20-trimethylsilyloxy-19-norpregna-5( 10),9(11)-diene (15).

Trimethylsilyl chloride (TMSCl, 10.6 mL, 83.5 mmol) was added dropwise to a solution of compound 14 (16.64 mmol) in dry pyridine (60 mL) under an inert atmosphere. The reaction mixture slowly warmed to room temperature over 2 h and was quenched with H$_2$O. The aqueous layer was extracted three times with EtOAc, washed with H$_2$O and brine, and dried over Na$_2$SO$_4$. The solvent was removed in vacuo. The compound was purified by flash column chromatography (3:1 hexanes/EtOAc) to give compound 15 (6.33 g) in 85% overall yield from 13. $^1$H NMR δ 5.58 (br s, 1, C-1I H), 3.95 (s, 4, ketal), 3.85 (q, 1, J=6.1 Hz, C-20 H), 2.24 (s, 1, ethynyl H), 1.22 (d, 3, J=6.2 Hz, C-21 H), 0.73 (s, 3, C-18 H), 0.11 (s, 9, $(CH_3)_3Si$).

3,3-[1,2-Ethanediylbis(oxy)]-17α-(1-propynyl)-20-trimethylsilyloxy-19-norpregna-5(10),9(11)-diene (16) (Method A).

Compound 15 (280 mg, 0.64 mmol) was dissolved in dry THF (3.5 mL) and cooled to −78° C. under argon. Then 1 mL of freshly prepared lithium diisopropylamide (LDA, 0.75 mmol) was added. The reaction mixture was stirred at −78° C. for 1.5 h and then MeI (0.2 mL, 3.2 mmol) was added. The reaction mixture slowly warmed to −40° C. over 2 h. The reaction was quenched with saturated $NH_4Cl$ and extracted twice with $CH_2Cl_2$. The organic layers were combined, washed with water and brine, and dried over $MgSO_4$. The solvent was removed in vacuo to yield a pale yellow oil. According to $^1$H NMR, 33% of the ethynyl compound was methylated. The product/starting material mixture was resubjected to the same conditions as above to increase the amount of desired product (16) in the mixture.

3,3-[1,2-Ethanediylbis(oxy)]-17α-(1-propynyl)-20-trimethylsilyloxy-19-norpregna-5(10),9(11)-diene (16) (Method B).

N-tert-Butyltrimethylsilylamine (6.2 mL, 32.5 mmol) dissolved in dry THF (31 mL) was cooled to −78° C. under an inert atmosphere. n-BuLi (13.0 mL, 32.5 mmol) was added over 3 min, turning the solution pale yellow. The anion was stirred for 20 min at −78° C. and then warmed to 0° C. over 40 min prior to use.

Compound 15 (5.7 g, 12.93 mmol) was dissolved in dry THF (40 mL) and was cooled to −78° C. under an inert atmosphere. Then 25 mL of freshly prepared anion solution from above (16.25 mmol) was added. The reaction mixture was stirred at −78° C. for 1.75 h and then MeI (5.0 mL, 80.34 mmol) was added. The reaction mixture slowly warmed over 2.25 h. The reaction was quenched with saturated $NH_4Cl$ and the mixture extracted four times with $CH_2Cl_2$. The organic layers were combined, washed with water and brine, and dried over $Na_2SO_4$. The solvent was removed in vacuo to yield a pale yellow solid. Purification by flash column chromatography (3:1 hexanes/EtOAc) afforded compound 16 (5.40 g) in 92% yield. $^1$H NMR δ 5.60 (br s, 1, C-11 H), 3.97 (s, 4, ketal), 3.82 (q, 1, J=6.1 Hz, C-20 H), 1.80 (s, 3, propynyl $CH_3$), 1.19 (d, 3, J=6.2 Hz, C-21 H), 0.72 (s, 3, C-18 H), 0.12 (s, 9, $(CH_3)_3Si$). MS (EI, m/z) 454 (M$^+$).

3,3-[1,2-Ethanediylbis(oxy)]-5,10α-oxido-17α(1-propynyl)-20-trimethylsilyloxy-19-norpregn-9(11)-ene (17).

Compound 16 (3.68 g, 8.1 mmol) dissolved in $CH_2Cl_2$ (80 mL) was cooled to 0° C. under an inert atmosphere, followed by the addition of solid $N_2HPO_4$ (575 mg, 4.05 mmol). After 5 min, hexafluoroacetone (0.63 mL, 4.5 mmol) and 50% $H_2O_2$ (1.10 mL, 16.2 mmol) were added. The reaction mixture was slowly warmed to room temperature overnight. The reaction was quenched with saturated $NaHCO_3$ and the mixture extracted three times with $CH_2Cl_2$. The organic layers were combined, washed with saturated $NaHCO_3$ and brine, and dried over $Na_2SO_4$. The solvent was removed in vacuo to yield a mixture of the α and β epoxides in a crude quantitative yield. The crude product was used in the next step. $^1$H NMR δ 6.02 (br s, 1, C-11 H), 3.92 (m, 4, ketal), 3.82 (d, 1, J=6.1 Hz, C-20 H), 1.80 (s, 3, propynyl $CH_3$), 1.18 (d, 3, J=6.2 Hz, C-18 H), 0.70 (s, 3, C-18 H), 0.10 (s, 9, $CH_3Si$).

11β-[4-(N,N-Dimethylamino)phenyl]-3,3-[1,2-ethanediylbis(oxy)]-5α-hydroxy-17α-(1-propynyl)-20-trimethylsilyloxy-19-norpregn-9-ene (18a).

CuCl (1.45 g, 14.64 mmol) was dissolved in dry THF (30 mL) and cooled to 0° C. under an inert atmosphere. A 2.0 M solution of freshly prepared Grignard reagent from 4-bromo-N,N-dimethylaniline (36.0 mL, 72 mmol) was added slowly. After 10 min, compound 17 (3.35 g, 7.12 mmol) in dry THF (35 mL) was added via cannula. The reaction mixture slowly warmed to room temperature over 1.5 h and was quenched with saturated $NH_4Cl$. The aqueous layer was extracted three times with EtOAc. The organic layers were combined, washed with saturated $NH_4Cl$ and brine, and dried over $Na_2SO_4$. The solvent was removed in vacuo to give a green solid. Purification by flash column chromatography (3:1 hexanes/EtOAc) afforded compound 18a (2.52 g) in 60% yield for two steps. $^1$H NMR δ 7.04 (d, 2, J=8.5 Hz, ArH), 6.62 (d, 2, J=8.8 Hz, ArH), 4.38 (s, 1, C-5 OH), 4.16 (br s, 1, C-11 H), 3.95 (m, 4, ketal), 3.68 (d, 1, J=6.1 Hz, C-20 H), 2.89 (s, 6, $(CH_3)_2N$), 1.86 (s, 3, propynyl $CH_3$), 1.14 (d, 3, J=6.2 Hz, C-21 H), 0.38 (s, 3, C-18 H), 0.11 (s, 9, $(CH_3)_3Si$).

11β-[4-(N,N-Dimethylamino)phenyl]-17α-(1-propynyl)-19-norpregna-4,9-dien-20-ol (19a).

Compound 18a (2.85 g, 4.81 mmol) was dissolved in $CH_2Cl_2$ (200 mL) and cooled to 0° C. Next, $H_2O$ (5 mL) and trifluoroacetic acid (TFA, 6 mL) were added. The reaction was quenched after 45 min with saturated $NaHCO_3$ and the mixture extracted twice with $CH_2Cl_2$. The organic layers were combined, washed with $H_2O$ and brine, and dried over $Na_2SO_4$. The solvent was removed in vacuo to yield a yellow solid. Purification by flash column chromatography (1:1 EtOAc/hexanes) gave compound 19a (1.9 g) in 86.4% yield. $^1$H NMR δ 7.02 (d, 2, J=8.6 Hz, ArH), 6.64 (d, 2, J=8.8 Hz, ArH), 5.75 (s, 1, C-4 H), 4.29 (br d, 1, J=6.6 Hz, C-11 H), 3.70 (d, 1, J=4.2, 6.1 Hzs, C-20 H), 2.90 (s, 6, $(CH_3)_2N$), 1.90 (s, 3, propynyl $CH_3$), 1.19 (d, 3, J=6.2 Hz, C-21 H), 0.51 (s, 3, C-18 H).

11β-[4-(N,N-Dimethylamino)phenyl]-17α-(1-propynyl)-19-norpregna-4,9-diene-3,20-dione (A-1).

Compound 19a (1.9 g, 4.15 mmol) was dissolved in DMSO (30 mL) and then solid o-iodoxybenzoic acid (IBX, 1.75 g, 6.25 mmol) was added. The reaction mixture was stirred overnight at room temperature. TLC indicated a mixture of product and starting material. The reaction was quenched with dilute $NaHCO_3$ (pH=9). The resulting mixture was extracted five times with ether. The organic layers were combined, washed with $H_2O$ and brine, and dried over $Na_2SO_4$. The solvent was removed in vacuo to yield a crude mixture of product and starting material. Purification and separation by flash column chromatography (2:1 hexanes/EtOAc) afforded compound A-1 (800 mg) in 43% yield and starting material 19a (500 mg, 26% recovery) was also isolated. For A-1: $^1$H NMR δ 7.00 (d, 2, J=8.6 Hz, ArH), 6.64 (d, 2, J=8.8Hz, ArH), 5.76 (s, 1, C-4 H), 4.39 (br d, 1, J=6.6Hz, C-11 H), 2.91 (s, 6, $(CH_3)_2N$), 2.29 (s, 3, C-21 H), 1.89 (s, 3, propynyl $CH_3$), 0.31 (s, 3, C-18 H).

This product was combined with a previous batch (total 900 mg) and purified by reverse phase preparative HPLC (85% MeOH: 15% $H_2O$ as eluent on a C-18 column) to yield 700 mg of A-1 that was greater than 97% pure by analytical HPLC. MS (EI, m/z) 455 (M$^+$). Anal. Calcd for $C_{31}H_{37}NO_2$: C, 81.72; H, 8.19; N, 3.07. Found C, 81.55, H, 8.24, N, 3.06.

Example 2

Synthesis of 11β-(4-Acetylphenyl)-17α-(1-propynyl)-19-norpregna-4,9-diene-3,20-dione (A-16).

3,3-[1,2-Ethanediylbis(oxy)]-11β-{4-{1,1-[1,2-ethanediylbis(oxy)]ethyl}phenyl}-5α-hydroxy-17α-(1-propynyl)-20-trimethylsilyloxy-19-norpregn-9-ene (18b).

CuCl (461 mg, 4.66 mmol) was stirred in dry THF (7 mL) and cooled to 0° C. under an inert atmosphere. A 0.5 M solution of freshly prepared Grignard reagent from p-bromoacetophenone ethylene ketal (46.1 mL, 23.0 mmol) was added slowly. After 10 min, epoxide 17 (1.095 g, 2.33 mmol) in dry THF (18 mL) was added via cannula. The reaction mixture slowly warmed to room temperature over 1.5 h and was quenched with saturated $NH_4Cl$ solution. The aqueous layer was extracted three times with EtOAc. The organic layers were combined, washed with water and brine, and dried over $Na_2SO_4$. The solvent was removed in vacuo. A crude purification by flash column chromatography (3:2 hexanes-EtOAc) afforded compound 18b which was used immediately in the next step.

11β-(4-Acetylphenyl)-20-hydroxy-17α-(1-propynyl)-19-norpregna-4,9-dien-3-one (19b).

Crude compound 18b (assumed 2.0 mmol) was dissolved in $CH_2Cl_2$ (100 mL) and cooled to 0° C. $H_2O$ (4 mL) and trifluoroacetic acid (3.0 mL) were added. The reaction was quenched after 1 h with saturated $NaHCO_3$ solution and the mixture extracted twice with $CH_2Cl_2$. The organic layers were combined, washed with water and brine, and dried over $Na_2SO_4$. The solvent was removed in vacuo to yield a greenish-yellow solid. Purification of the solid by flash column chromatography (3:2 EtOAc-hexanes) afforded compound 19b (690 mg) in 62% yield for three steps. $^1H$ NMR δ 7.87 (d, 2, J=8.2 Hz, ArH), 7.29 (d, 2, J=8.0 Hz, ArH), 5.79 (s, 1, C-4 H), 4.40 (d, 1, J=5.9 Hz, C-11αH), 3.68 (m, 1, C-20 H), 2.57 (s, 3, arylacetyl $CH_3$), 1.92 (s, 3, propynyl $CH_3$), 1.20 (d, 3, J=6.1 Hz, C-21 H), 0.45 (s, 3, C-18 H).

11β-(4-Acetylphenyl)-17α-(1-propynyl)-19-norpregna-4,9-diene-3,20-dione (A-16).

Compound 19b (690 mg, 1.51 mmol) was dissolved in dry DMSO (15 mL) and then solid o-iodoxybenzoic acid (IBX) (2.95 g, 10.53 mmol) was added. The reaction mixture was stirred overnight at room temperature. The reaction did not go to completion. The mixture was diluted with $H_2O$ and extracted four times with ether. The organic layers were combined, washed with water and brine, and dried over $Na_2SO_4$. The solvent was removed in vacuo to give an orange solid. Purification by flash column chromatography (3:2 EtOAc-hexanes) afforded compound A-16 (480 mg) in 70% yield and some recovered starting material. The compound was further purified by preparative HPLC (80% MeOH/20% $H_2O$) to afford compound A-16 as a white solid that was greater than 97% pure: mp 113–118° C.; $^1H$ NMR δ 7.88 (d, 2, J=8.4Hz, ArH), 7.28 (d, 2, J=8.5 Hz, ArH), 5.80 (s, 1, C-4 H), 4.50 (d, 1, J=7.7 Hz, C-11αH), 2.57 (s, 3, arylacetyl $CH_3$), 2.28 (s, 3, C-21 H), 1.90 (s, 3, propynyl $CH_3$), 0.25 (s, 3, C-18 H). MS (EI, m/z) 454 ($M^+$). Anal. Calcd for $C_{31}H_{34}O_3$·0.25 $H_2O$: C, 81.10; H, 7.57. Found C, 81.15; H,7.60.

Example 3

Synthesis of 11β-[4-(Methylthio)phenyl]-17α-(1-propynyl)-19-norpregna-4,9-diene-3,20-dione (A-31).

3,3-[1,2-Ethanediylbis(oxy)]-5α-hydroxy-11β-[4-(methylthio)phenyl]-17α-(1-propynyl)-20-trimethylsilyloxy-19-norpregn-9-ene (18c).

CuCl (400 mg, 4.0 mmol) was stirred in dry THF (8 mL) and cooled to 0° C. under an inert atmosphere. A 1.0 M solution of freshly prepared Grignard reagent from 4-bromothioanisole (20.0 mL, 20 mmol) was added slowly. After 10 minutes, crude compound 17 (assumed 2.0 mmol) in dry THF (15 mL) was added via cannula. The reaction mixture slowly warmed to room temperature over 1.5 h and was quenched with saturated $NH_4Cl$ solution. The aqueous layer was extracted three times with EtOAc. The organic layers were combined, washed with saturated $NH_4Cl$ and brine, and dried over $Na_2SO_4$. The solvent was removed in vacuo. Quick purification by flash column chromatography (3:1 hexanes-EtOAc) afforded compound 18c, which was used immediately in the next step.

11β-[4-(Methylthio)phenyl]-20-hydroxy-17α-(1-propynyl)-19-norpregna-4,9-dien-3-one (19c).

Compound 18c (assumed 2.0 mmol) was dissolved in $CH_2Cl_2$ (80 mL) and cooled to 0° C. $H_2O$ (3 mL) and trifluoroacetic acid (2.5 mL) were added. The reaction was quenched after 1 h with saturated $NaHCO_3$ solution and the mixture extracted three times with $CH_2Cl_2$. The organic layers were combined, washed with water and brine, and dried over $MgSO_4$. The solvent was removed in vacuo. Purification of the residue by flash column chromatography (1:2 EtOAc-hexanes) afforded compound 19c (495 mg) in 46% yield for three steps. $^1H$ NMR δ 7.15 (d, 2, J=8.7 Hz, ArH), 7.09 (d, 2, J=8.5 Hz, ArH), 5.76 (s, 1 C-4 H), 4.32 (d, 1, J=6.6 Hz, C-11αH), 3.69 (br t, 1, C-20 H), 2.45 (s, 3, $SCH_3$), 1.91 (s, 3, propynyl $CH_3$), 1.19 (d, 3, J=6.15Hz, C-21 H), 0.48 (s, 3, C-18H).

11β-[4-(Methylthio)phenyl]-17α-(1-propynyl)-19-norpregna-4,9-diene-3,20-dione (A-31).

Compound 19c (495 mg, 1.07 mmol) was dissolved in dry DMSO (15 mL) and then solid IBX (1.5 g, 5.36 mmol) was added. The reaction mixture was stirred overnight at room temperature. The reaction was quenched with $H_2O$ and the mixture extracted four times with ether. The organic layers were combined, washed with water and brine, and dried over $Na_2SO_4$. The solvent was removed in vacuo. Purification of the residue by flash column chromatography (3:2 hexanes-EtOAc) afforded compound A-31 that was less than 97% pure by analytical HPLC. Further purification by preparative HPLC (85% MeOH-15% $H_2O$) afforded pure A-31 (340 mg) in 69% yield: mp 164–167.5° C.; $^1H$ NMR δ 7.16 (d, 2, J=8.5 Hz, ArH), 7.08 (d, 2, J=8.5 Hz, ArH), 5.78 (s, 1, C-4 H), 4.35 (d, 1, J=7.3 Hz, C-11αH), 2. (s, 3, $SCH_3$), 2.28 (s, 3, C-21 H), 1.89 (s, 3, propynyl $CH_3$), 0.28 (s, 3, C-18 H). MS (EI, m/z) 458 ($M^+$). Anal. Calcd for $C_{30}H_{34}O_2S$: C, 78.56; H, 7.47; S, 6.99. Found C, 78.48; H, 7.50, S, 6.91.

The biological activity of the compounds of this invention was examined by means of in vitro and in vivo tests.

Receptor Binding. The affinity of the compounds for hormone receptors was determined by standard procedures similar to those that have been described, inter alia, by Wagner et al., Proc. Natl. Acad. Sci., 93, 8739–8744 (1996) for COS-1 cells. The human breast carcinoma (T-47D) cell line was used to assess RBA for progestin receptor. The cell line used was obtained from ATCC (American Type Culture Collection) and stored frozen at −135° C. until a week before the assays were conducted. The cells were thawed and cultured to achieve the desired cell number (5 to 7 days on average). They were maintained at 37° C. with growth media until they were 90–100% confluent, at which time they were recovered from the growth flasks and dispersed into individual wells of a 12-well tissue culture plate at a count of $4.0 \times 10^5$ cells in one mL of medium per well. After 24 h, the cells adhered to the bottom of the 12-well plates. At this point, the receptor binding assay procedure was initiated by the addition of test or standard compounds with $^3$H-R5020 (promegestone). After incubation overnight, medium was removed, the cells were washed and solubilized and radio-activity was measured by liquid scintillation spectrometry. Nonspecific binding was determined by incubation with an excess of unlabeled R5020 and subtracted from total binding to calculate specific binding.

The progesterone binding assay was conducted with several concentrations of the reference standard (promegestone, R-5020) and an internal standard (progesterone). These hormones were allowed to compete with tritiated competitor ($^3$H-promegestone, $^3$H-R5020) to estimate relative binding. Test steroids were tested at three or more concentrations. If 50% displacement of the $^3$HR5020 from the receptor was not achieved by the unknown, higher or lower concentrations were tested, as needed, to obtain that goal. All compounds were tested in duplicate by at least two assays.

The percentage of specifically bound $^3$H-R5020 for each concentration tested was calculated and binding curves were generated by plotting the percentage of specifically bound $^3$H-R-5020 versus the concentration of the competitor. The relative binding activity (RBA) of the test compounds, relative to the reference standard (R5020) as well as the internal standard, was determined from the ratio of concentrations causing 50% displacement for each unknown and standard, and expressed as a percentage value. These concentrations were obtained by graphical interpolation of the plots. When this was done, it was found that the compound 11β-[4-(N,N-dimethylamino)phenyl]-17α-(1-propynyl)-19-norpregna-4,9-diene-3,20-dione (A-1) had an RBA of 313% that of R-5020. The analogous compound 11β-[4-acetylphenyl]-17α-(1-propynyl)-19-norpregna-4,9-diene-3,20-dione (A-16) had an RBA of 439% that of R-5020.

In vivo Test. Antiprogestational activity was determined in vivo by dose-response studies in estrogen-primed, progesterone-stimulated immature female rabbits and results were scored according to McPhail (McPhail, J. Physiol., 83: 146 (1934)). These are standard procedures well-known to those skilled in the art. For determining antiprogestational (antagonist) activity, the test compound was given orally together with subcutaneous administration of progesterone. It was tested orally at 0.5, 1 and 2 mg total dose in estrogenprimed immature female rabbits that were simultaneously given subcutaneous progesterone. The rabbits, weighing about 1.5 kg, were primed with estrogen one a day for 6 days and then treated once a day for 5 days with 0.8 mg total dose of progesterone—i.e. 160 μg/day—while at the same time giving the test compound orally once a day in a vehicle of 10% ethanol/sesame oil (0.5 mL volume). Necropsy was performed one day after the last dose. Uterine endometrial effects were scored according to McPhail and potency was evaluated by statistical comparison with the standard compound 17α-acetoxy-11β-[4-(N,N-dimethylamino)phenyl]-19-norpregna-4,9-diene-3,20-dione. Surprisingly, introduction of the 17α-propynyl moiety resulted in an exceptionally potent antiprogestational response, as the compound 11β-[4-(N,N-dimethylamino)phenyl]-17α-(1-propynyl)-19-norpregna-4,9-diene-3,20-dione (A-1) upon oral administration was 5-fold as potent as the standard compound. In turn (see C. E. Cook et al, Human Reproduction, 9, Supplement 1, 32–39, June 1994) the standard compound is approximately 3-fold as potent as the drug mifepristone, which is currently used in humans for its antiprogestational activity, making the propynyl compound of this invention as much as 15-fold as potent as mifepristone.

The analogous compound 11β-(4-acetylphenyl)-17α-(1-propynyl)-19-norpregna-4,9-diene-3,20-dione (A-16) also had antiprogestational activity, and was 0.15 to 0.23-fold as potent as the standard compound. The much lower potency compared with that of the standard and particularly that of the dimethylamino analog in the face of high binding affinity for the progestin receptor suggests that compound A-16 has agonist activity, as well as modest antagonist activity.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound of structure I,

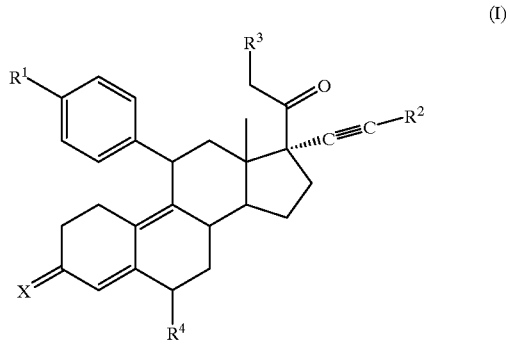

where $R^1$ is $(CH_3)_2N$—, $CH_3NH$—, $NH_2$—;

$R^2$ is $CH_3$—, $CF_3$—, $HOCH_2$—;

$R^3$ is H—, $CH_3$—, $CH_3O$—, $CH_3COO$—;

$R^4$ is H—, $CH_3$—, F—, Cl—; and

X is O, (H,H), NOH, NOCH$_3$, and pharmnaccutically acceptable salts thereof.

2. The compound of claim 1, of formula III

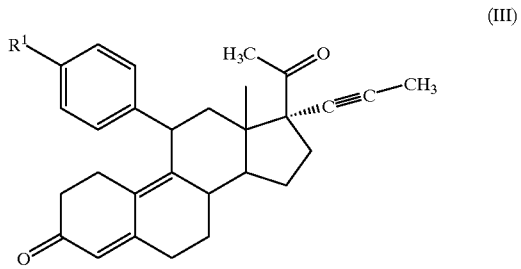

where $R^1$ is $(CH_3)_2N$—, $CH_3NH$—, $NH_2$—.

3. The compound of claim 1, formula IV

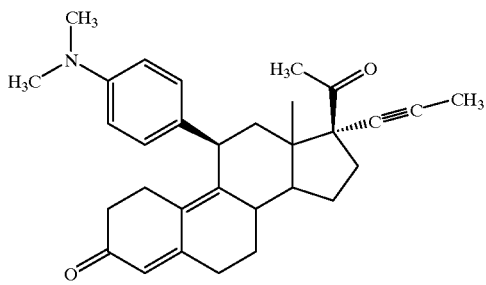

(IV)

4. The steroid of claim 1 selected from the group consisting of:

11β-(4-aminophenyl)-17α-(1-propynyl)-19-norpregna-4,9-diene-3,20-dione;

11β-(4-aminophenyl)-17α-(3,3,3-trifluoropropyn-1-yl)-19-norpregna-4,9-diene-3,20-dione;

11β-(4-aminophenyl)-17α-(3-hydroxypropyn-1-yl)-19-norpregna-4,9-diene-3,20-dione;

11β-(4-aminophenyl)-21-methoxy-17α-(1-propynyl)-19-norpregna-4,9-diene-3,20-dione;

11β-(4-aminophenyl)-21-methoxy-17α-(3,3,3-trifluoropropyn-1-yl)-19-norpregna-4,9-diene-3,20-dione;

11β-(4-aminophenyl)-21-methoxy-17α-(3-hydroxypropyn-1-yl)-19-norpregna-4,9-diene-3,20-dione;

11β-(4-aminophenyl)-21-methoxy-3-oximino-17α-(1-propynyl)-19-norpregna-4,9-diene-3,20-dione;

11β-(4-aminophenyl)-21-methoxy-3-oximino-17α-(3,3,3-trifluoropropyn-1-yl)-19-norpregna-4,9-diene-3,20-dione;

11β-(4-aminophenyl)-21-methoxy-3-oximino-17α-(3-hydroxypropyn-1-yl)-19-norpregna-4,9-diene-3,20-dione;

11β-(4-aminophenyl)-21-methoxy-6-fluoro-17α-(1-propynyl)-19-norpregna-4,9-diene-3,20-dione;

11β-(4-aminophenyl)-21-methoxy-6-fluoro-17α-(3,3,3-trifluoropropyn-1-yl)-19-norpregna-4,9-diene-3,20-dione;

11β-(4-aminophenyl)-21-methoxy-6-fluoro-17α-(3-hydroxypropyn-1-yl)-19-norpregna-4,9-diene-3,20-dione;

11β-(4-aminophenyl)-21-methoxy-6-fluoro-3-oximino-17α-(1-propynyl)-19-norpregna-4,9-diene-3,20-dione;

11β-(4-aminophenyl)-21-methoxy-6-fluoro-3-oximino-17α-(3,3,3-trifluoropropyn-1-yl)-19-norpregna-4,9-diene-3,20-dione;

11β-(4-aminophenyl)-21-methoxy-6-fluoro-3-oximino-17α-(3-hydroxypropyn-1-yl)-19-norpregna-4,9-diene-3,20-dione;

11β-(4-aminophenyl)-21-methoxy-6-methyl-17α-(1-propynyl)-19-norpregna-4,9-diene-3,20-dione;

11β-(4-aminophenyl)-21-methoxy-6-methyl-17α-(3,3,3-trifluoropropyn-1-yl)-19-norpregna-4,9-diene-3,20-dione;

11β-(4-aminophenyl)-21-methoxy-6-methyl-17α-(3-hydroxypropyn-1-yl)-19-norpregna-4,9-diene-3,20-dione;

11β-(4-aminophenyl)-21-methoxy-6-methyl-3-oximino-17α-(1-propynyl)-19-norpregna-4,9-diene-3,20-dione;

11β-(4-aminophenyl)-21-methoxy-6-methyl-3-oximino-17α-(3,3,3-trifluoropropyn-1-yl)-19-norpregna-4,9-diene-3,20-dione;

11β-(4-aminophenyl)-21-methoxy-6-methyl-3-oximino-17α-(3-hydroxypropyn-1-yl)-19-norpregna-4,9-diene-3,20-dione;

11β-(4-aminophenyl)-21-methyl-17α-(1-propynyl)-19-norpregna-4,9-diene-3,20-dione;

11β-(4-aminophenyl)-21-methyl-17α-(3,3,3-trifluoropropyn-1-yl)-19-norpregna-4,9-diene-3,20-dione;

11β-(4-aminophenyl)-21-methyl-17α-(3-hydroxypropyn-1-yl)-19-norpregna-4,9-diene-3,20-dione;

11β-(4-aminophenyl)-21-methyl-3-oximino-17α-(1-propynyl)-19-norpregna-4,9-diene-3,20-dione;

11β-(4-aminophenyl)-21-methyl-3-oximino-17α-(3,3,3-trifluoropropyn-1-yl)-19-norpregna-4,9-diene-3,20-dione;

11β-(4-aminophenyl)-21-methyl-3-oximino-17α-(3-hydroxypropyn-1-yl)-19-norpregna-4,9-diene-3,20-dione;

11β-(4-aminophenyl)-21-methyl-6-fluoro-17α-(1-propynyl)-19-norpregna-4,9-diene-3,20-dione;

11β-(4-aminophenyl)-21-methyl-6-fluoro-17α-(3,3,3-trifluoropropyn-1-yl)-19-norpregna-4,9-diene-3,20-dione;

11β-(4-aminophenyl)-21-methyl-6-fluoro-17α-(3-hydroxypropyn-1-yl)-19-norpregna-4,9-diene-3,20-dione;

11β-(4-aminophenyl)-21-methyl-6-fluoro-3-oximino-17α-(1-propynyl)-19-norpregna-4,9-diene-3,20-dione;

11β-(4-aminophenyl)-21-methyl-6-fluoro-3-oximino-17α-(3,3,3-trifluoropropyn-1-yl)-19-norpregna-4,9-diene-3,20-dione;

11β-(4-aminophenyl)-21-methyl-6-fluoro-3-oximino-17α-(3-hydroxypropyn-1-yl)-19-norpregna-4,9-diene-3,20-dione;

11β-(4-aminophenyl)-6,21-dimethyl-17α-(1-propynyl)-19-norpregna-4,9-diene-3,20-dione;

11β-(4-aminophenyl)-6,21-dimethyl-17α-(3,3,3-trifluoropropyn-1-yl)-19-norpregna-4,9-diene-3,20-dione;

11β-(4-aminophenyl)-6,21-dimethyl-17α-(3-hydroxypropyn-1-yl)-19-norpregna-4,9-diene-3,20-dione;

11β-(4-aminophenyl)-6,21-dimethyl-3-oximino-17α-(1-propynyl)-19-norpregna-4,9-diene-3,20-dione;

11β-(4-aminophenyl)-6,21-dimethyl-3-oximino-17α-(3,3,3-trifluoropropyn-1-yl)-19-norpregna-3,20-dione;

11β-(4-aminophenyl)-6,21-dimethyl-3-oximino-17α-(3-hydroxypropyn-1-yl)-19-norpregna-4,9-diene-3,20-dione;

11β-(4-aminophenyl)-3-oximino-17α-(1-propynyl)-19-norpregna-4,9-diene-3,20-dione;

11β-(4-aminophenyl)-3-oximino-17α-(3,3,3-trifluoropropyn-1-yl)-19-norpregna-4,9-diene-3,20-dione;

11β-(4-aminophenyl)-3-oximino-17α-(3-hydroxypropyn-1-yl)-19-norpregna-4,9-diene-3,20-dione;

11β-(4-aminophenyl)-6-fluoro-17α-(1-propynyl)-19-norpregna-4,9-diene-3,20-dione;

11β-(4-aminophenyl)-6-fluoro-17α-(3,3,3-trifluoropropyn-1-yl)-19-norpregna-4,9-diene-3,20-dione;

11β-(4-aminophenyl)-6-fluoro-17α-(3-hydroxypropyn-1-yl)-19-norpregna-4,9-diene-3,20-dione;

11β-(4-aminophenyl)-6-fluoro-3-oximino-17α-(1-propynyl)-19-norpregna-4,9-diene-3,20-dione;

11β-(4-aminophenyl)-6-fluoro-3-oximino-17α-(3,3,3-trifluoropropyn-1-yl)-19-norpregna-4,9-diene-3,20-dione;

11β-(4-aminophenyl)-6-fluoro-3-oximino-17α-(3-hydroxypropyn-1-yl)-19-norpregna-4,9-diene-3,20-dione;

11β-(4-aminophenyl)-6-methyl-17α-(1-propynyl)-19-norpregna-4,9-diene-3,20-dione;

11β-(4-aminophenyl)-6-methyl-17α-(3,3,3-trifluoropropyn-1-yl)-19-norpregna-4,9-diene-3,20-dione;

11β-(4-aminophenyl)-6-methyl-17α-(3-hydroxypropyn-1-yl)-19-norpregna-4,9-diene-3,20-dione;

11β-(4-aminophenyl)-6-methyl-3-oximino-17α-(1-propynyl)-19-norpregna-4,9-diene-3,20-dione;

11β-(4-aminophenyl)-6-methyl-3-oximino-17α-(3,3,3-trifluoropropyn-1-yl)-19-norpregna-4,9-diene-3,20-dione;

1-(4-aminophenyl)-6-methyl-3-oximino-17α-(3-hydroxypropyn-1-yl)-19-norpregna-4,9-diene-3,20-dione;

11β-[4-(N,N-dimethylamino)phenyl]-17α-(1-propynyl)-19-norpregna-4,9-diene-3,20-dione;

11β-[4-(N,N-dimethylamino)phenyl]-17α-(3,3,3-trifluoropropyn-1-yl)-19-norpregna-4,9-diene-3,20-dione;

11β-[4-(N,N-dimethylamino)phenyl]-17α-(3-hydroxypropyn-1-yl)-19-norpregna-4,9-diene-3,20-dione;

11β-[4-(N,N-dimethylamino)phenyl]-21-methoxy-17α-(1-propynyl)-19-norpregna-4,9-diene-3,20-dione;

11β-[4-(N,N-dimethylamino)phenyl]-21-methoxy-17α-(3,3,3-trifluoropropyn-1-yl)-19-norpregna-4,9-diene-3,20-dione;

11β-[4-(N,N-dimethylamino)phenyl]-21-methoxy-17α-(3-hydroxypropyn-1-yl)-19-norpregna-4,9-diene-3,20-dione;

11β-[4-(N,N-dimethylamino)phenyl]-21-methoxy-3-oximino-17α-(1-propynyl)-19-norpregna-4,9-diene-3,20-dione;

11β-[4-(N,N-dimethylamino)phenyl]-21-methoxy-3-oximino-17α-(3,3,3-trifluoropropyn-1-yl)-19-norpregna-4,9-diene-3,20-dione;

11β-[4-(N,N-dimethylamino)phenyl]-21-methoxy-3-oximino-17α-(3-hydroxypropyn-1-yl)-19-norpregna-4,9-diene-3,20-dione;

11β-[4-(N,N-dimethylamino)phenyl]-21-methoxy-6-fluoro-17α-(1-propynyl)-19-norpregna-4,9-diene-3,20-dione;

11β-[4-(N,N-dimethylamino)phenyl]-21-methoxy-6-fluoro-17α-(3,3,3-trifluoropropyn-1-yl)-19-norpregna-4,9-diene-3,20-dione;

11β-[4-(N,N-dimethylamino)phenyl]-21-methoxy-6-fluoro-17α-(3-hydroxypropyn-1-yl)-19-norpregna-4,9-diene-3,20-dione;

11β-[4-(N,N-dimethylamino)phenyl]-21-methoxy-6-fluoro-3-oximino-17α-(1-propynyl)-19-norpregna-4,9-diene-3,20-dione;

11β-[4-(N,N-dimethylamino)phenyl]-21-methoxy-6-fluoro-3-oximino-17α-(3,3,3-trifluoropropyn-1-yl)-19-norpregna-4,9-diene-3,20-dione;

11β-[4-(N,N-dimethylamino)phenyl]-21-methoxy-6-fluoro-3-oximino-17α-(3-hydroxypropyn-1-yl)-19-norpregna-4,9-diene-3,20-dione;

11β-[4-(N,N-dimethylamino)phenyl]-21-methoxy-6-methyl-17α-(1-propynyl)-19-norpregna-4,9-diene-3,20-dione;

11β-[4-(N,N-dimethylamino)phenyl]-21-methoxy-6-methyl-17α-(3,3,3-trifluoropropyn-1-yl)-19-norpregna-4,9-diene-3,20-dione;

11β-[4-(N,N-dimethylamino)phenyl]-21-methoxy-6-methyl-17α-(3-hydroxypropyn-1-yl)-19-norpregna-4,9-diene-3,20-dione;

11β-[4-(N,N-dimethylamino)phenyl]-21-methoxy-6-methyl-3-oximino-17α-(1-propynyl)-19-norpregna-4,9-diene-3,20-dione;

11β-[4-(N,N-dimethylamino)phenyl]-21-methoxy-6-methyl-3-oximino-17α-(3,3,3-trifluoropropyn-1-yl)-19-norpregna-4,9-diene-3,20-dione;

11β-[4-(N,N-dimethylamino)phenyl]-21-methoxy-6-methyl-3-oximino-17α-(3-hydroxypropyn-1-yl)-19-norpregna-4,9-diene-3,20-dione;

11β-[4-(N,N-dimethylamino)phenyl]-21-methyl-17α-(1-propynyl)-19-norpregna-4,9-diene-3,20-dione;

11β-[4-(N,N-dimethylamino)phenyl]-21-methyl-17α-(3,3,3-trifluoropropyn-1-yl)-19-norpregna-4,9-diene-3,20-dione;

11β-[4-(N,N-dimethylamino)phenyl]-21-methyl-17α-(3-hydroxypropyn-1-yl)-19-norpregna-4,9-diene-3,20-dione;

11β-[4-(N,N-dimethylamino)phenyl]-21-methyl-3-oximino-17α-(1-propynyl)-19-norpregna-4,9-diene-3,20-dione;

11β-[4-(N,N-dimethylamino)phenyl]-21-methyl-3-oximino-17α-(3,3,3-trifluoropropyn-1-yl)-19-norpregna-4,9-diene-3,20-dione;

11β-[4-(N,N-dimethylamino)phenyl]-21-methyl-3-oximino-17α-(3-hydroxypropyn-1-yl)-19-norpregna-4,9-diene-3,20-dione;

11β-[4-(N,N-dimethylamino)phenyl]-21-methyl-6-fluoro-17α-(1-propynyl)-19-norpregna-4,9-diene-3,20-dione;

11β-[4-(N,N-dimethylamino)phenyl]-21-methyl-6-fluoro-17α-(3,3,3-trifluoropropyn-1-yl)-19-norpregna-4,9-diene-3,20-dione;

11β-[4-(N,N-dimethylamino)phenyl]-21-methyl-6-fluoro-17α-(3-hydroxypropyn-1-yl)-19-norpregna-4,9-diene-3,20-dione;

11β-[4-(N,N-dimethylamino)phenyl]-21-methyl-6-fluoro-3-oximino-17α-(1-propynyl)-19-norpregna-4,9-diene-3,20-dione;

11β-[4-(N,N-dimethylamino)phenyl]-21-methyl-6-fluoro-3-oximino-17α-(3,3,3-trifluoropropyn-1-yl)-19-norpregna-4,9-diene-3,20-dione;

11β-[4-(N,N-dimethylamino)phenyl]-21-methyl-6-fluoro-3-oximino-17α-(3-hydroxypropyn-1-yl)-19-norpregna-4,9-diene-3,20-dione;

11β-[4-(N,N-dimethylamino)phenyl]-6,21-dimethyl-17α-(1-propynyl)-19-norpregna-4,9-diene-3,20-dione;

11β-[4-(N,N-dimethylamino)phenyl]-6,21-dimethyl-17α-(3,3,3-trifluoropropyn-1-yl)-19-norpregna-4,9-diene-3,20-dione;

11β-[4-(N,N-dimethylamino)phenyl]-6,21-dimethyl-17α-(3-hydroxypropyn-1-yl)-19-norpregna-4,9-diene-3,20-dione;

11β-[4-(N,N-dimethylamino)phenyl]-6,21-dimethyl-3-oximino-17α-(1-propynyl)-19-norpregna-4,9-diene-3,20-dione;

11β-[4-(N,N-dimethylamino)phenyl]-6,21-dimethyl-3-oximino-17α-(3,3,3-trifluoropropyn-1-yl)-19-norpregna-4,9-diene-3,20-dione;

11β-[4-(N,N-dimethylamino)phenyl]-6,21-dimethyl-3-oximino-17α-(3-hydroxypropyn-1-yl)19-norpregna-4,9-diene-3,20-dione;

11β-[4-(N,N-dimethylamino)phenyl]-3-oximino-17α-(1-propynyl)-19-norpregna-4,9-diene-3,20-dione;

11β-[4-(N,N-dimethylamino)phenyl]-3-oximino-17α-(3,3,3-trifluoropropyn-1-yl)-19-norpregna-4,9-diene-3,20-dione;

11β-[4-(N,N-dimethylamino)phenyl]-3-oximino-17α-(3-hydroxypropyn-1-yl)-19-norpregna-4,9-diene-3,20-dione;

11β-[4-(N,N-dimethylamino)phenyl]-6-fluoro-17α-(1-propynyl)-19-norpregna-4,9-diene-3,20-dione;

11β-[4-(N,N-dimethylamino)phenyl]-6-fluoro-17α-(3,3,3-trifluoropropyn-1-yl)-19-norpregna-4,9-diene-3,20-dione;

11β-[4-(N,N-dimethylamino)phenyl]-6-fluoro-17α-(3-hydroxypropyn-1-yl)-19-norpregna-4,9-diene-3,20-dione;

11β-[4-(N,N-dimethylamino)phenyl]-6-fluoro-3-oximino-17α-(1-propynyl)-19-norpregna-4,9-diene-3,20-dione;

11β-[4-(N,N-dimethylamino)phenyl]-6-fluoro-3-oximino-17α-(3,3,3-trifluoropropyn-1-yl)-19-norpregna-4,9-diene-3,20-dione;

11β-[4-(N,N-dimethylamino)phenyl]-6-fluoro-3-oximino-17α-(3-hydroxypropyn-1-yl)-19-norpregna-4,9-diene-3,20-dione;

11β-[4-(N,N-dimethylamino)phenyl]-6-methyl-17α-(1-propynyl)-19-norpregna-4,9-diene-3,20-dione;

11β-[4-(N,N-dimethylamino)phenyl]-6-methyl-17α-(3,3,3-trifluoropropyn-1-yl)-19-norpregna-4,9-diene-3,20-dione;

11β-[4-(N,N-dimethylamino)phenyl]-6-methyl-17α-(3-hydroxypropyn-1-yl)-19-norpregna-4,9-diene-3,20-dione;

11β-[4-(N,N-dimethylamino)phenyl]-6-methyl-3-oximino-17α-(1-propynyl)-19-norpregna-4,9-diene-3,20-dione;

11β-[4-(N,N-dimethylamino)phenyl]-6-methyl-3-oximino-17α-(3,3,3-trifluoropropyn-1-yl)-19-norpregna-4,9-diene-3,20-dione;

11β-[4-(N,N-dimethylamino)phenyl]-6-methyl-3-oximino-17α-(3-hydroxypropyn-1-yl)-19-norpregna-4,9-diene-3,20-dione;

11β-[4-(N-methylamino)phenyl]-17α-(1-propynyl)-19-norpregna-4,9-diene-3,20-dione;

11β-[4-(N-methylamino)phenyl]-17α-(3,3,3-trifluoropropyn-1-yl)-19-norpregna-4,9-diene-3,20-dione;

11β-[4-(N-methylamino)phenyl]-17α-(3-hydroxypropyn-1-yl)-19-norpregna-4,9-diene-3,20-dione;

11β-[4-(N-methylamino)phenyl]-21-methoxy-17α-(1-propynyl)-19-norpregna-4,9-diene-3,20-dione;

11β-[4-(N-methylamino)phenyl]-21-methoxy-17α-(3,3,3-trifluoropropyn-1-yl)-19-norpregna-4,9-diene-3,20-dione;

11β-[4-(N-methylamino)phenyl]-21-methoxy-17α-(3-hydroxypropyn-1-yl)-19-norpregna-4,9-diene-3,20-dione;

11β-[4-(N-methylamino)phenyl]-21-methoxy-3-oximino-17α-(1-propynyl)- 19-norpregna-4,9-diene-3,20-dione;

11-[4-(N-methylamino)phenyl]-21-methoxy-3-oximino-17α-(3,3,3-trifluoropropyn-1-yl)-19-norpregna-4,9-diene-3,20-dione;

11-[4-(N-methylamino)phenyl]-21-methoxy-3-oximino-17α-(3-hydroxypropyn-1-yl)-19-norpregna-4,9-diene-3,20-dione;

11β-[4-(N-methylamino)phenyl]-21-methoxy-6-fluoro-17α-(1-propynyl)-19-norpregna-4,9-diene-3,20-dione;

11-[4-(N-methylamino)phenyl]-21-methoxy-6-fluoro-17α-(3,3,3-trifluoropropyn-1-yl)-19-norpregna-4,9-diene-3,20-dione;

11β-[4-(N-methylamino)phenyl]-21-methoxy-6-fluoro-17α-(3-hydroxypropyn-1-yl)-19-norpregna-4,9-diene-3,20-dione;

11β-[4-(N-methylamino)phenyl]-21-methoxy-6-fluoro-3-oximino-17α-(1-propynyl)-19-norpregna-4,9-diene-3,20-dione;

11β-[4-(N-methylamino)phenyl]-21-methoxy-6-fluoro-3-oximino-17α-(3,3,3-trifluoropropyn-1-yl)-19-norpregna-4,9-diene-3,20-dione;

11-[4-(N-methylamino)phenyl]-21-methoxy-6-fluoro-3-oximino-17α-(3-hydroxypropyn-1-yl)-19-norpregna-4,9-diene-3,20-dione;

11β-[4-(N-methylamino)phenyl]-21-methoxy-6-methyl-17α-(1-propynyl)-19-norpregna-4,9-diene-3,20-dione;

11β-[4-(N-methylamino)phenyl]-21-methoxy-6-methyl-17α-(3,3,3-tri fluoropropyn-1-yl)-19-norpregna-4,9-diene-3,20-dione;

11β-[4-(N-methylamino)phenyl]-21-methoxy-6-methyl-17α-(3-hydroxypropyn-1-yl)-19-norpregna-4,9-diene-3,20-dione;

11β-[4-(N-methylamino)phenyl]-21-methoxy-6-methyl-3-oximino-17α-(1-propynyl)-19-norpregna-4,9-diene-3,20-dione;

11β-[4-(N-methylamino)phenyl]-21-methoxy-6-methyl-3-oximino-17α-(3,3,3-trifluoropropyn-1-yl)-19-norpregna-4,9-diene-3,20-dione;

11β-[4-(N-methylamino)phenyl]-21-methoxy-6-methyl-3-oximino-17α-(3-hydroxypropyn-1-yl)-19-norpregna-4,9-diene-3,20-dione;

11β-[4-(N-methylamino)phenyl]-21-methyl-17α-(1-propynyl)-19-norpregna-4,9-diene-3,20-dione;

11β-[4-(N-methylamino)phenyl]-21-methyl-17α-(3,3,3-trifluoropropyn-1-yl)-19-norpregna-4,9-diene-3,20-dione;

11β-[4-(N-methylamino)phenyl]-21-methyl-17α-(3-hydroxypropyn-1-yl)-19-norpregna-4,9-diene-3,20-dione;

11β-[4-(N-methylamino)phenyl]-21-methyl-3-oximino-17α-(1-propynyl)-19-norpregna-4,9-diene-3,20-dione;

11β-[4-(N-methylamino)phenyl]-21-methyl-3-oximino-17α-(3,3,3-trifluoropropyn-1-yl)-19-norpregna-4,9-diene-3,20-dione;

11β-[4-(N-methylamino)phenyl]-21-methyl-3-oximino-17α-(3-hydroxypropyn-1-yl)-19-norpregna-4,9-diene-3,20-dione;

11β-[4-(N-methylamino)phenyl]-21-methyl-6-fluoro-17α-(1-propynyl)-19-norpregna-4,9-diene-3,20-dione;

11β-[4-(N-methylamino)phenyl]-21-methyl-6-fluoro-17α-(3,3,3-trifluoropropyn-1-yl-19-norpregna-4,9-diene-3,20-dione;

11β-[4-(N-methylamino)phenyl]-21-methyl-6-fluoro-17α-(3-hydroxypropyn-1-yl)- 19-norpregna-4,9-diene-3,20-dione;

11β-[4-(N-methylamino)phenyl]-21-methyl-6-fluoro-3-oximino-17α-(1-propynyl)-19-norpregna-4,9-diene-3,20-dione;

11β-[4-(N-methylamino)phenyl]-21-methyl-6-fluoro-3-oximino-17α-(3,3,3-trifluoropropyn-1-yl)-19-norpregna-4,9-diene-3,20-dione;

11β-[4-(N-methylamino)phenyl]-21-methyl-6-fluoro-3-oximino-17α-(3-hydroxypropyn-1-yl)-19-norpregna-4,9-diene-3,20-dione;

11β-[4-(N-methylamino)phenyl]-6,21-dimethyl-17α-(1-propynyl)-19-norpregna-4,9-diene-3,20-dione;

11β-[4-(N-methylamino)phenyl]-6,21-dimethyl-17α-(3,3,3-trifluoropropyn-1-yl)-19-norpregna-4,9-diene-3,20-dione;

11β-[4-(N-methylamino)phenyl]-6,21-dimethyl-17α-(3-hydroxypropyn-1-yl)-19-norpregna-4,9-diene-3,20-dione;

11β-[4-(N-methylamino)phenyl]-6,21-dimethyl-3-oximino-17α-(1-propynyl)-19-norpregna-4,9-diene-3,20-dione;

11β-[4-(N-methylamino)phenyl]-6,21-dimethyl-3-oximino-17α-(3,3,3-trifluoropropyn-1-yl)-19-norpregna-4,9-diene-3,20-dione;

11β-[4-(N-methylamino)phenyl]-6,21-dimethyl-3-oximino-17α-(3-hydroxypropyn-1-yl)-19-norpregna-4,9-diene-3,20-dione;

11β-[4-(N-methylamino)phenyl]-3-oximino-17α-(1-propynyl)-19-norpregna-4,9-diene-3,20-dione;

11β-[4-(N-methylamino)phenyl]-3-oximino-17α-(3,3,3-trifluoropropyn-1-yl)-19-norpregna-4,9-diene-3,20-dione;

11β-[4-(N-methylamino)phenyl]-3-oximino-17α-(3-hydroxypropyn-1-yl)-19-norpregna-4,9-diene-3,20-dione;

11β-[4-(N-methylamino)phenyl]-6-fluoro-17α-(1-propynyl)-19-norpregna-4,9-diene-3,20-dione;

11β-[4-(N-methylamino)phenyl]-6-fluoro-17α-(3,3,3-trifluoropropyn-1-yl)-19-norpregna-4,9-diene-3,20-dione;

11β-[4-(N-methylamino)phenyl]-6-fluoro-17α-(3-hydroxypropyn-1-yl)-19-norpregna-4,9-diene-3,20-dione;

11β-[4-(N-methylamino)phenyl]-6-fluoro-3-oximino-17α-(1-propynyl)-19-norpregna-4,9-diene-3,20-dione;

11β-[4-(N-methylamino)phenyl]-6-fluoro-3-oximino-17α-(3,3,3-trifluoropropyn-1-yl)-19-norpregna-4,9-diene-3,20-dione;

11β-[4-(N-methylamino)phenyl]-6-fluoro-3-oximino-17α-(3-hydroxypropyn-1-yl)-19-norpregna-4,9-diene-3,20-dione;

11β-[4-(N-methylamino)phenyl]-6-methyl-17α-(1-propynyl)-19-norpregna-4,9-diene-3,20-dione;

11β-[4-(N-methylamino)phenyl]-6-methyl-17α-(3,3,3-trifluoropropyn-1-yl)-19-norpregna-4,9-diene-3,20-dione;

11β-[4-(N-methylamino)phenyl]-6-methyl-17α-(3-hydroxypropyn-1-yl)-19-norpregna-4,9-diene-3,20-dione;

11β-[4-(N-methylamino)phenyl]-6-methyl-3-oximino-17α-(1-propynyl)-19-norpregna-4,9-diene-3,20-dione;

11β-[4-(N-methylamino)phenyl]-6-methyl-3-oximino-17α-(3,3,3-trifluoropropyn- 1-yl)-19-norpregna-4,9-diene-3,20-dione;

11β-[4-(N-methylamino)phenyl]-6-methyl-3-oximino-17α-(3-hydroxypropyn-1-yl)-19-norpregna-4,9-diene-3,20-dione;

21-acetoxy-11β-(4-aminophenyl)-17α-(1-propynyl)-19-norpregna-4,9-diene-3,20-dione;

21-acetoxy-11β-(4-aminophenyl)-17α-(3,3,3-trifluoropropyn-1-yl)-19-norpregna-4,9-diene-3,20-dione;

21-acetoxy-11β-(4-aminophenyl)-17α-(3-hydroxypropyn-1-yl)-19-norpregna-4,9-diene-3,20-dione;

21-acetoxy-11β-(4-aminophenyl)-3-oximino-17α-(1-propynyl)-19-norpregna-4,9-diene-3,20-dione;

21-acetoxy-11β-(4-aminophenyl)-3-oximino-17α-(3,3,3-trifluoropropyn-1-yl)-19-norpregna-4,9-diene-3,20-dione;

21-acetoxy-11β-(4-aminophenyl)-3-oximino-17α-(3-hydroxypropyn-1-yl)-19-1:5 norpregna-4,9-diene-3,20-dione;

21-acetoxy-11β-(4-aminophenyl)-6-fluoro-17α-(1-propynyl)-19-norpregna-4,9-diene-3,20-dione;

21-acetoxy-11β-(4-aminophenyl)-6-fluoro-17α-(3,3,3-trifluoropropyn-1-yl)-19-norpregna-4,9-diene-3,20-dione;

21-acetoxy-11β-(4-aminophenyl)-6-fluoro-17α-(3-hydroxypropyn-1-yl)-19-norpregna-4,9-diene-3,20-dione;

21-acetoxy-11β-(4-aminophenyl)-6-fluoro-3-oximino-17α-(1-propynyl)-19-norpregna-4,9-diene-3,20-dione;

21-acetoxy-11β-(4-aminophenyl)-6-fluoro-3-oximino-17α-(3,3,3-trifluoropropyn-1-yl)-19-norpregna-4,9-diene-3,20-dione;

21-acetoxy-11β-(4-aminophenyl)-6-fluoro-3-oximino-17α-(3-hydroxypropyn-1-yl)-19-norpregna-4,9-diene-3,20-dione;

21-acetoxy-11β-(4-aminophenyl)-6-methyl-17α-(1-propynyl)-19-norpregna-4,9-diene-3,20-dione;

21-acetoxy-11β-(4-aminophenyl)-6-methyl-17α-(3,3,3-trifluoropropyn-1-yl)-19-norpregna-4,9-diene-3,20-dione;

21-acetoxy-11β-(4-aminophenyl)-6-methyl-17α-(3-hydroxypropyn-1-yl)-19-norpregna-4,9-diene-3,20-dione;

21-acetoxy-11β-(4-aminophenyl)-6-methyl-3-oximino-17α-(1-propynyl)-19-norpregna-4,9-diene-3,20-dione;

21-acetoxy-11β-(4-aminophenyl)-6-methyl-3-oximino-17α-(3,3,3-trifluoropropyn-1-yl)-19-norpregna-4,9-diene-3,20-dione;

21-acetoxy-11β-(4-aminophenyl)-6-methyl-3-oximino-17α-(3-hydroxypropyn-1-yl)-19-norpregna-4,9-diene-3,20-dione;

21-acetoxy-11β-[4-(N,N-dimethylamino)phenyl]-17α-(1-propynyl)-19-norpregna-4,9-diene-3,20-dione;

21-acetoxy-11β-[4-(N,N-dimethylamino)phenyl]-17α-(3,3,3-trifluoropropyn-1-yl)-19-norpregna-4,9-diene-3,20-dione;

21-acetoxy-11β-[4-(N,N-dimethylamino)phenyl]-17α-(3-hydroxypropyn-1-yl)-19-norpregna-4,9-diene-3,20-dione;

21-acetoxy-11β-[4-(N,N-dimethylamino)phenyl]-3-oximino-17α-(1-propynyl)-19-norpregna-4,9-diene-3,20-dione;

21-acetoxy-11β-[4-(N,N-dimethylamino)phenyl]-3-oximino-17α-(3,3,3-trifluoropropyn-1-yl)-19-norpregna-4,9-diene-3,20-dione;

21-acetoxy-11β-[4-(N,N-dimethylamino)phenyl]-3-oximino-17α-(3-hydroxypropyn-1-yl)-19-norpregna-4,9-diene-3,20-dione;

21-acetoxy-11β-[4-(N,N-dimethylamino)phenyl]-6-fluoro-17α-(1-propynyl)-19-norpregna-4,9-diene-3,20-dione;

21-acetoxy-11β-[4-(N,N-dimethylamino)phenyl]-6-fluoro-17α-(3,3,3-trifluoropropyn-1-yl)-19-norpregna-4,9-diene-3,20-dione;

21-acetoxy-11β-[4-(N,N-dimethylamino)phenyl]-6-fluoro-17α-(3-hydroxypropyn-1-yl)-19-norpregna-4,9-diene-3,20-dione;

21-acetoxy-11β-[4-(N,N-dimethylamino)phenyl]-6-fluoro-3-oximino-17α-(1-propynyl)-19-norpregna-4,9-diene-3,20-dione;

21-acetoxy-11β-[4-(N,N-dimethylamino)phenyl]-6-fluoro-3-oximino-17α-(3,3,3-trifluoropropyn-1-yl)-19-norpregna-4,9-diene-3,20-dione;

21-acetoxy-11β-[4-(N,N-dimethylamino)phenyl]-6-fluoro-3-oximino-17α-(3-hydroxypropyn-1-yl)-19-norpregna-4,9-diene-3,20-dione;

21-acetoxy-11β-[4-(N,N-dimethylamino)phenyl]-6-methyl-17α-(1-propynyl)-19-norpregna-4,9-diene-3,20-dione;

21-acetoxy-11β-[4-(N,N-dimethylamino)phenyl]-6-methyl-17α-(3,3,3-trifluoropropyn-1-yl)-19-norpregna-4,9-diene-3,20-dione;

21-acetoxy-11β-[4-(N,N-dimethylamino)phenyl]-6-methyl-17α-(3-hydroxypropyn-1-yl)-19-norpregna-4,9-diene-3,20-dione;

21-acetoxy-11β-[4-(N,N-dimethylamino)phenyl]-6-methyl-3-oximino-17α-(1-propynyl)-19-norpregna-4,9-diene-3,20-dione;

21-acetoxy-11β-[4-(N,N-dimethylamino)phenyl]-6-methyl-3-oximino-17α-(3,3,3-trifluoropropyn-1-yl)-19-norpregna-4,9-diene-3,20-dione;

21-acetoxy-11β-[4-(N,N-dimethylamino)phenyl]-6-methyl-3-oximino-17α-(3-hydroxypropyn-1-yl)-19-norpregna-4,9-diene-3,20-dione;

21-acetoxy-11β-[4-(N-methylamino)phenyl]-17α-(1-propynyl)-19-norpregna-4,9-diene-3,20-dione;

21-acetoxy-11β-[4-(N-methylamino)phenyl]-17α-(3,3,3-trifluoropropyn-1-yl)-19-norpregna-4,9-diene-3,20-dione;

21-acetoxy-11β-[4-(N-methylamino)phenyl]-17α-(3-hydroxypropyn-1-yl)-19-norpregna-4,9-diene-3,20-dione;

21-acetoxy-11β-[4-(N-methylamino)phenyl]-3-oximino-17α-(1-propynyl)-19-norpregna-4,9-diene-3,20-dione;

21-acetoxy-11β-[4-(N-methylamino)phenyl]-3-oximino-17α-(3,3,3-trifluoropropyn-1-yl)-19-norpregna-4,9-diene-3,20-dione;

21-acetoxy-1β-[4-(N-methylamino)phenyl]-3-oximino-17α-(3-hydroxypropyn-1-yl)-19-norpregna-4,9-diene-3,20-dione;

21-acetoxy-11β-[4-(N-methylamino)phenyl]-6-fluoro-17α-(1-propynyl)-19-norpregna-4,9-diene-3,20-dione;

21-acetoxy-11β-[4-(N-methylamino)phenyl]-6-fluoro-17α-(3,3,3-trifluoropropyn-1-yl)-19-norpregna-4,9-diene-3,20-dione;

21-acetoxy-11β-[4-(N-methylamino)phenyl]-6-fluoro-17α-(3-hydroxypropyn-1-yl)-19-norpregna-4,9-diene-3,20-dione;

21-acetoxy-11β-[4-(N-methylamino)phenyl]-6-fluoro-3-oximino-17α-(1-propynyl)-19-norpregna-4,9-diene-3,20-dione;

21-acetoxy-11β-[4-(N-methylamino)phenyl]-6-fluoro-3-oximino-17α-(3-hydroxypropyn-1-yl)-19-norpregna-4,9-diene-3,20-dione;

21-acetoxy-11β-[4-(N-methylamino)phenyl]-6-fluoro-3-oximino-17α-(3,3,3-trifluoropropyn-1-yl)-19-norpregna-4,9-diene-3,20-dione;

21-acetoxy-11β-[4-(N-methylamino)phenyl]-6-methyl-17α-(1-propynyl)-19-norpregna-4,9-diene-3,20-dione;

21-acetoxy-11β-[4-(N-methylamino)phenyl]-6-methyl-17α-(3,3,3-trifluoropropyn-1-yl)-19-norpregna-4,9-diene-3,20-dione;

21-acetoxy-11β-[4-(N-methylamino)phenyl]-6-methyl-17α-(3-hydroxypropyn-1-yl)-19-norpregna-4,9-diene-3,20-dione;

21-acetoxy-11β-[4-(N-methylamino)phenyl]-6-methyl-3-oximino-17α-(1-propynyl)-19-norpregna-4,9-diene-3,20-dione;

21-acetoxy-11β-[4-(N-methylamino)phenyl]-6-methyl-3-oximino-17α-(3-hydroxypropyn-1-yl)-19-norpregna-4,9-diene-3,20-dione; and 21-acetoxy-11β-[4-(N-methylamino)phenyl]-6-methyl-3-oximino-17α-(3,3,3-trifluoropropyn-1-yl)-19-norpregna-4,9-diene-3,20-dione.

5. A method of treating the antiprogestational activity comprising administering a therapeutically effective amount of the compound of claim 1, to a patient in need thereof.

\* \* \* \* \*